United States Patent
Zhang et al.

(10) Patent No.: US 11,696,687 B2
(45) Date of Patent: Jul. 11, 2023

(54) DYNAMIC INTERACTION-ORIENTED SUBJECT'S LIMB TIME-VARYING STIFFNESS IDENTIFICATION METHOD AND DEVICE

(71) Applicant: HUAZHONG UNIVERSITY OF SCIENCE AND TECHNOLOGY, Hubei (CN)

(72) Inventors: Qin Zhang, Hubei (CN); Jihan Liu, Hubei (CN); Yusheng Chen, Hubei (CN); Caihua Xiong, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 0 days.

(21) Appl. No.: 17/858,028

(22) Filed: Jul. 5, 2022

(65) Prior Publication Data
US 2023/0028793 A1 Jan. 26, 2023

(30) Foreign Application Priority Data

Jul. 15, 2021 (CN) .......................... 202110798706.7

(51) Int. Cl.
*A61B 5/00* (2006.01)
*G06T 7/70* (2017.01)
*A61B 5/107* (2006.01)
(Continued)

(52) U.S. Cl.
CPC .......... *A61B 5/0057* (2013.01); *A61B 5/1071* (2013.01); *A61B 5/1126* (2013.01);
(Continued)

(58) Field of Classification Search
CPC ..... A61B 34/00; A61B 5/0057; A61B 5/1071; A61B 5/1126
See application file for complete search history.

(56) References Cited

PUBLICATIONS

Yang, Chenguang, et al. "Interface design of a physical human-robot interaction system for human impedance adaptive skill transfer." IEEE Transactions on Automation Science and Engineering 15.1 (2017): 329-340. (Year: 2017).*

(Continued)

*Primary Examiner* — Alex M Valvis
*Assistant Examiner* — Yasmeen S Warsi
(74) *Attorney, Agent, or Firm* — JCIPRNET

(57) ABSTRACT

The disclosure provides a dynamic interaction-oriented subject's limb time-varying stiffness identification method and device. The method includes: the combination of subject's limb displacement and measured force data or the combination of angle and measured torque data is collected; based on the time-varying dynamic system constructed based on a second-order impedance model, the linear parameter varying method is utilized to substitute the time-varying impedance parameters and reconstruct the restoring force/torque expression; iterative identification is performed on variable weights, dynamic interaction force/torque, and restoring force/torque by using time-varying dynamic parameters based on the dynamic interaction force/torque expression expanded from basis function; the time-varying stiffness is solved by using variable weights and dynamic interaction force/torque according to expression with substituted the time-varying impedance parameters. The disclosure not only improves the accuracy of the time-varying stiffness identification technology but also expands the application scenarios of the time-varying stiffness identification technology.

11 Claims, 3 Drawing Sheets

(51) Int. Cl.
*A61B 5/11* (2006.01)
*B25J 9/16* (2006.01)
*B25J 13/08* (2006.01)
*G06T 7/20* (2017.01)
*A61B 34/00* (2016.01)
*A61B 90/00* (2016.01)
*A61B 90/50* (2016.01)

(52) U.S. Cl.
CPC ........... *B25J 9/1633* (2013.01); *B25J 9/1653* (2013.01); *B25J 13/085* (2013.01); *G06T 7/20* (2013.01); *G06T 7/70* (2017.01); *A61B 34/00* (2016.02); *A61B 90/50* (2016.02); *A61B 2090/064* (2016.02); *G06T 2207/30196* (2013.01); *G06T 2207/30204* (2013.01)

(56) References Cited

PUBLICATIONS

Rouse, Elliott J., et al. "Estimation of human ankle impedance during the stance phase of walking." IEEE Transactions on Neural Systems and Rehabilitation Engineering 22.4 (2014): 870-878. (Year: 2014).*

Lee, Hyunglae, and Neville Hogan. "Time-varying ankle mechanical impedance during human locomotion." IEEE Transactions on Neural Systems and Rehabilitation Engineering 23.5 (2014): 755-764. (Year: 2014).*

* cited by examiner

DYNAMIC INTERACTION-ORIENTED SUBJECT'S LIMB TIME-VARYING STIFFNESS IDENTIFICATION METHOD AND DEVICE

CROSS-REFERENCE TO RELATED APPLICATION

This application claims the priority benefit of China application serial no. 202110798706.7, filed on Jul. 15, 2021. The entirety of the above-mentioned patent application is hereby incorporated by reference herein and made a part of this specification.

BACKGROUND

Technical Field

The disclosure belongs to the field of limb stiffness measurement, and more particularly, relates to a dynamic interaction-oriented subject's limb time-varying stiffness identification method and device.

Description of Related Art

In performing a variety of movements in daily life, such as movement using lower limb, e.g., walking, running, and going up and down stairs, or movement using upper limb, e.g., catching a ball and lifting heavy objects, biological individuals can always show excellent movement stability, and which is achievable due to abundant of tissue compositions of biological individuals and the fast and efficient neural regulation mechanism. When the limbs of biological individuals interact dynamically with the environment or objects, their central nervous systems will adjust the stiffness characteristics of the limbs according to different task requirements, so as to maintain the stability of the limbs or joints during the dynamic interaction.

Current stiffness research is divided into two categories, namely time-invariant stiffness research and time-varying stiffness research. Time-invariant stiffness research assumes that the stiffness of biological individuals does not change with time. Clearly, this process does not conform to the characteristics of real-time changes in stiffness of biological individuals in the process of dynamic interaction with the environment or objects. Therefore, studying the time-varying stiffness characteristics of biological individuals is not only helpful to explore the adjustment mechanism of biological individual's time-varying stiffness, introducing the biological individual's time-varying stiffness regulation mechanism into the study of human-computer interaction control, adaptive variable impedance control, and variable impedance driver of the robot system may also significantly improve the performance of robotic systems. The identification of the time-varying stiffness of biological individuals is the premise of this kind of research, and it is very important to propose a fast and accurate time-varying stiffness identification algorithm for dynamic interaction.

At present, the time-varying stiffness identification techniques include short data segments method, ensemble-based method, linear parameter varying method and basis function expansion method. Among the above methods, the short data segments method is to divide the non-stationary data set into a large number of quasi-stationary short data segments that are identified as time-invariant system parameters, and then group the short data segments with similar quasi-stationary characteristics and identify them with a time-invariant model, so as to get the time-varying stiffness. Since the short data segments method is based on the assumption of quasi-stationary short segment data, such premise makes it only suitable for identifying slowly changing limb stiffness characteristics, and it is not possible to obtain the global time-varying characteristics of limb stiffness. The ensemble-based method adopts hundreds of experimental data with the same time-varying characteristics to construct ensemble data, and then uses a time-invariant model estimated from the ensemble data at the same moment to describe the characteristics of the time-varying system at that moment. It can be seen that the key to the identification method based on ensemble data is to conduct a large number of experiments with the same time-varying characteristics. It can be easily found that the short data segments method and the ensemble-based method have the same characteristics, that is, they both need to identify the time-varying stiffness parameters based on a large number of data sets with the same time-varying behavior. Such characteristic requires a lengthy experiment process, a large amount of data and the consistency of multiple time-varying behaviors is difficult to be ensured.

Different from the above two methods, the linear parameter varying method and the basis function expansion method can directly identify the time-varying stiffness of the limbs through data from a single experiment. Among the above methods, the linear parameter varying method models the time-varying system parameters as a function with one or more time-varying scheduling variables as independent variables. The premise of this approach is to determine that the scheduling variables directly affect the time-varying characteristics of the system, and the scheduling variable must be available either directly or indirectly. The basis function expansion method is to directly model the time-varying system parameters as a weighted sum of a series of basis functions with time independent variables. After the form of basis function is determined, the method converts the time-invariant system equation into the time-invariant system method which takes the time-invariant weight value of each order basis function as the unknown parameter. After these unknown parameters are identified by the time-invariant system identification method, the original time-invariant system parameters can be synthesized. The limitation of the above two identification methods is that they can only be applied in situations where the limbs do not interact with the environment.

SUMMARY

The existing short data segments method and ensemble-based method require a large number of data sets with time-varying behavior to identify time-varying stiffness parameters, which makes it difficult to ensure the consistency of multiple time-varying behaviors. Meanwhile, the linear parameter varying method and the basis function expansion method are only suitable for situations where the limbs do not interact with the environment. Therefore, in view of the defects of the conventional technology, the purpose of the present disclosure is to provide a dynamic interaction-oriented subject's limb time-varying stiffness identification method and device, which aims to solve the problem that the current time-varying stiffness identification technology is not accurate enough and the lack of applicability in the occasion with dynamic interaction.

In order to achieve the above purpose, on the one hand, the present disclosure provides a dynamic interaction-oriented subject's limb time-varying stiffness identification method, including the following steps:

In the random small-perturbation motion environment, the subject keeps the limb posture unchanged, and by changing the activation states of muscles, the combination of the subject's limb displacement and measured force data or the combination of angle and measured torque data is collected.

Based on the expression of restoring force/torque with the substituted time-varying impedance parameters and the expression of dynamic interaction force/torque expanded by basis functions, and according to the combination of the subject's limb displacement and measured force data or the combination of angle and measured torque data, iterative identification to decouple dynamic interaction force/torque and restoring force/torque are performed by using parameters of time-varying dynamics.

The linear coefficient matrix and dynamic interaction force/torque obtained in the iterative identification of parameters are utilized to calculate the time-varying stiffness of the subject's limb according to the restoring force/torque expression with the substituted time-varying impedance parameters.

Specifically, the method for collecting the combination of the subject's limb displacement and measured force data or the combination of angle and measured torque data is as follows.

In the three-dimensional space random small-perturbation motion environment constructed by the collaborative robotic arm, the subject's limbs and the end of the collaborative robotic arm are firmly connected together.

A certain number of reflective markers are fixed on the end of the collaborative robotic arm, and an optical motion capture system will collect the three-dimensional positions of the reflective markers to obtain the displacement/angle information of the subject's limbs.

A certain number of reflective markers will be fixed on the end of subject's limbs or limbs and torso with adjacent joints in order to record the limb posture.

The end of the robotic arm is connected with a six-dimensional force/torque sensor to collect the force/torque information between the subject's limb and the end of the robotic arm.

A display is placed directly in front of the subject to display the changes of force/torque of the six-dimensional force/torque sensor on the end of the robotic arm during the experiment, providing visual feedback for the subject's limbs.

During the acquisition of the time-varying stiffness data of the subject's limbs, under the random small-perturbation motion environment established by the collaborative robotic arm, the limb endpoints or joints of the subject are fixedly connected to the collaborative robotic arm, keeping the limb posture unchanged, and the time-varying stiffness of the subject's limb is changed by changing the activation states of the muscles.

The time-varying stiffness is reflected by the interaction force/torque recorded by the six-dimensional force/torque sensor at the end of the collaborative robotic arm. In the three directions (or rotation axes) of X, Y, and Z, the positive interaction force/torque is increased first and then decreased, and then the negative interaction force/torque is increased and then decreased. In this manner, the force/torque cycle in three directions (or rotation axis) is completed, and which is a dynamic force/torque interaction cycle.

Within the specified perturbation duration interval, the subject's limb needs to complete at least one dynamic force/torque transformation cycle, and the completion time of each cycle is not limited.

The displacement/angle information and force/torque information of the subject's limb collected according to the above method may be used to identify the time-varying stiffness of the subject's limbs.

Specifically, the method for obtaining the expression of the restoring force/torque with substituted time-varying parameter includes the following steps.

According to the time-varying impedance characteristics of the subject's limb, the second-order impedance model is used to construct the subject's limb time-varying dynamic system, and the expression thereof is:

$$I\ddot{x}(t)+B(t)\dot{x}(t)+K(t)x(t)=f_r(t) \quad (1)$$

In the expression, I is the inertial parameter of the subject's limb; B(t) is the time-varying damping parameter of the subject's limb; K(t) is the time-varying stiffness parameter of the subject's limb; x(t) is the displacement/angle of the subject's limb collected by the optical motion capture system; $f_r(t)$ is the restoring force/torque data of the subject's limb; $\dot{x}(t)$ is the first-order derivative of displacement/angle of the subject's limb; $\ddot{x}(t)$ is the second-order derivative of displacement/angle of the subject's limb; and t is time.

The linear parameter varying method is adopted to construct the time-varying damping parameter of the subject's limb and the time-varying stiffness parameter of the subject's limb in the dynamic model as the weighted sum of function with the scheduling variable dynamic interaction force/torque as the independent variable, and the expression thereof is:

$$K(t) = \sum_{i=0}^{P} a_i g_i(f_v(t)) \ B(t) = \sum_{i=0}^{P} b_i g_i(f_v(t)) \quad (2)$$

In the expression, B(t) is the time-varying damping parameter of the subject's limb, K(t) is the time-varying stiffness parameter of the subject's limb, $g_i(f_v(t))$ is the function with the dynamic interaction force/torque $f_v(t)$ as the independent variable, $a_i$ and $b_i$ are the weights of the i-th-order function, P is the maximum order of the function; and t is time.

The expression of the time-varying dynamics model of the subject's limb based on the expression with substituted time-varying impedance parameters is:

$$I\ddot{x}(t) + \sum_{i=0}^{P} b_i g_i(f_v(t))\dot{x}(t) + \sum_{i=0}^{P} a_i g_i(f_v(t))x(t) = f_r(t) \quad (3)$$

In the expression, I is the inertial parameter of the subject's limb, $g_i(f_v(t))$ is the function with dynamic interaction force/torque $f_v(t)$ as the independent variable, $a_i$ and $b_i$ are the weights of the i-th-order function, P is the maximum order of the function, $f_r(t)$ is the restoring force/torque of the subject's limb, x(t) is the displacement/angle of the subject's limb collected by the optical motion capture system, $\dot{x}(t)$ is the first-order derivative of the displacement/angle of the subject's limb, $\ddot{x}(t)$ is the second-order derivative of the displacement/angle of the subject's limb; and t is time.

The intermediate variables $x_g(i, t)$ and $\dot{x}_g(i, t)$ are constructed, and expressions are:

$$x_g(i,t)=g_i(f_v(t))x(t) \quad \dot{x}_g(i,t)=g_i(f_v(t))\dot{x}(t) \qquad (4)$$

In the expressions, $x_g(i, t)$ is the intermediate variable constructed by the function $g_i(f_v(t))$ and the displacement/angle $x(t)$ of the subject's limb, $g_i(f_v(t))$ is a function using dynamic interaction force/torque $f_v(t)$ as independent variable, $\dot{x}_g(i, t)$ is the intermediate variable constructed by the function $g_i(f_v(t))$ and the first-order derivative $\dot{x}(t)$ of the displacement/angle of the subject's limb, i is the order of the $g_i$ function, and t is time.

Based on the above expressions and variables that substitute time-varying impedance parameters, the expression of the reconstructed restoring force/torque is:

$$f_r(t)=\varphi(t)\beta \varphi(t)=[\ddot{x}(t)\dot{x}_g(0,t)\dot{x}_g(1,t) \ldots \dot{x}_g(P,t)x_g(0,t)x_g(1,t) \ldots x_g(P,t)]\beta=[I\ b_0 b_1 \ldots b_p a_0 a_1 \ldots a_P]^T \qquad (5)$$

In the expression, I is the inertial parameter of the subject's limb, $g_i(f_v(t))$ is the function with dynamic interaction force/torque $f_v(t)$ as the independent variable, $a_0 \ldots a_p$ and $b_0 \ldots b_p$ are the weights of the 0 ... P-th-order function, P is the maximum order of the function, $f_r(t)$ is the restoring force/torque of the subject's limb, $x(t)$ is the displacement/angle of the subject's limb collected by the optical motion capture system, $\beta$ is a linear coefficient matrix composing of the inertial parameters I of the subject's limbs and the weights $a_0 \ldots a_p$ and $b_0 \ldots b_p$ of the 0 ... P-th-order function, $\varphi(t)$ is the displacement/angle parameter matrix consisting of the variables $x_g(i, t)$ and $\dot{x}_g(i, t)$, and the second-order derivative $\ddot{x}(t)$ of the displacement/angle of subject's limb, $x_g(i, t)$ is an intermediate variable constructed from the function $g_i(f_v(t))$ and the displacement/angle $x(t)$ of the subject's limb, $\dot{x}_g(i, t)$ is an intermediate variable constructed from the function $g_i(f_v(t))$ and the first-order derivative $\dot{x}(t)$ of the displacement/angle of the subject's limb, i is the order of the $g_i$ function, and t is time.

Specifically, the dynamic interaction force/torque is expanded by the basis function, and the basis function sequence in the perturbation duration interval and the weights of the basis function are used to represent the dynamic interaction force/torque, and the expression is:

$$f_v(t) = \sum_{j=0}^{Q} c_j h_j(t) \qquad (6)$$

In the expression, $f_v(t)$ is the dynamic interaction force, $h_j(t)$ is the basis function sequence in the perturbation duration interval, $c_j$ represents the weight of the j-th-order basis function, Q is the maximum order of the basis function; and t is time.

Preferably, the method for iterative identification to decouple dynamic interaction force/torque and restoring force/torque using time-varying dynamic parameters includes the following steps:

(1) The collected subject's limb displacement is combined with the measured force data or the angle is combined with the measured torque data, and initialize the estimated value of the initial restoring force/torque as 0.

(2) Based on the combination of subject's limb displacement and measured force data or the combination of angle and measured torque data, combined with the estimated value of restoring force/torque under the current iteration, and according to the fact that the measured force/torque is equal to the sum of restoring force/torque and dynamic interaction force/torque, the intermediate variable of dynamic interaction force/torque is obtained.

(3) According to the expression of the dynamic interaction force/torque expanded by the basis function, the intermediate variable of the dynamic interaction force/torque is utilized to identify the weights of the basis function.

(4) The estimated value of the dynamic interaction force/torque under the current iteration is obtained by using the weights of the basis function and the sequence of basis functions in the perturbation duration interval.

(5) According to the fact that the measured force/torque is equal to the sum of the restoring force/torque and the dynamic interaction force/torque, the intermediate variable of the restoring force/torque is obtained.

(6) Based on the expression of restoring force/torque with substituted time-varying impedance parameters, the intermediate variable of restoring force/torque is utilized to obtain a linear coefficient matrix.

(7) According to the displacement parameter matrix and the linear coefficient matrix obtained under the current iteration, the estimated value of the restoring force/torque under the current iteration is obtained.

(8) Return to step (2) until the actual number of iterations reaches the predetermined maximum number of iterations, and the linear coefficient matrix, the estimated value of restoring force/torque and the estimated value of dynamic interaction force/torque obtained in the last iteration are output.

Specifically, the expression of each step of the method for iterative identification to decouple dynamic interaction force/torque and restoring force/torque using time-varying dynamic parameters is:

Step: (1): Initialization is performed, $f_m(t)$, $x(t)$, $\dot{x}(t)$ and $\ddot{x}(t)$ are known, and set the initial estimated value of $f_r(t)$ as $\hat{f}_r^0(t)=0$.

Steps (2), (3), and (4): For the n-th iteration, the intermediate variable $\hat{f}_v^{temp}(t)=f_m(t)-\hat{f}_r^{n-1}(t)$ is calculated, and set $$\hat{f}_v^{temp}(t) = \sum_{j=0}^{Q} c_j h_j(t)$$

according to formula (6), so as to identify the weight $c_j$, and the estimated value $\hat{f}_v^n(t)$ of obtained $f_v(t)$ is reconstructed.

Steps (5), (6), and (7): The intermediate variable $\hat{f}_r^{temp}(t)=f_m(t)-\hat{f}_v^n(t)$ is calculated, according to formula (4) and formula (5), set $\hat{f}_r^{temp}(t)=\varphi(t)\beta$, so as to identify the parameter $\beta$, and the estimated value $\hat{f}_r^n(t)$ of obtained $f_r(t)$ is reconstructed.

Step (8): Set n=n+1, go back to step 2 until n exceeds the set maximum number of iterations, then the iteration is terminated.

In the expression, $f_m(t)$ is the measured force/torque, $f_v(t)$ is the dynamic interaction force/torque, $f_r(t)$ is the restoring force/torque, $\hat{f}_r^0(t)$ is the initial value of the restoring force/torque, $\hat{f}_v^{temp}(t)$ is the intermediate variable, $\hat{f}_r^{n-1}(t)$ is the estimated value of the restoring force/torque in the n−1-th iteration, $\hat{f}_r^{temp}(t)$ is the intermediate variable, $\beta$ is the linear coefficient matrix composing of the inertial parameters I of the subject's limb, the weights $a_0 \ldots a_p$ and $b_0 \ldots b_p$ of the 0 ... P-th-order function, $\varphi(t)$ is the displacement/angle parameter matrix composing of the variables $x_g(i, t)$, $\dot{x}_g(i, t)$, and the second-order derivative $\ddot{x}(t)$ of the displacement/angle of the subject's limb, $\hat{f}_m^n(t)$ is the estimated value of measured force/torque of the n-th iteration, $\hat{f}_v^n(t)$ is the estimated value of the dynamic interaction force/torque of the n-th iteration, $\hat{f}_r^n(t)$ is the estimated value of the restoring force/torque of the n-th iteration; i and j are the order of the function, and t is time.

The linear coefficient matrix and the dynamic interaction force/torque obtained in the iterative identification process of the parameters are utilized, the time-varying stiffness of the subject's limbs is calculated according to the restoring force/torque expression with substituted time-varying impedance parameters.

In another aspect, the present disclosure provides a dynamic interaction-oriented subject's limb time-varying stiffness identification device, including: a data acquisition system, a restoring force/torque acquisition system, an iterative parameter identification system, and a dynamic interaction force/torque acquisition system.

The data acquisition system is configured to collect the combination of the subject's limb displacement and measured force data or the combination of angle and measured torque data by changing the activation states of muscles in the random small-perturbation motion environment, and the subject keeps the limb posture unchanged.

The restoring force/torque acquisition system is configured to reconstruct the expression of restoring force/torque by substituting the time-varying impedance parameters of the subject's limb with a linear parameter varying method according to the time-varying dynamic model of the subject's limb.

The iterative parameter identification system is configured to, based on the expression of restoring force/torque with substituted time-varying impedance parameters and the expression of dynamic interaction force/torque expanded by basis functions, and according to the combination of the subject's limb displacement and measured force data or the combination of angle and measured torque data, perform iterative identification to decouple dynamic interaction force/torque and restoring force/torque.

The dynamic interaction force/torque acquisition system is configured to expand the dynamic interaction force/torque using the basis functions, and the dynamic interaction force/torque is represented by the basis function sequence in the perturbation duration interval and the weights of the basis functions.

Preferably, the data acquisition system includes a collaborative robotic arm, reflective markers, an optical motion capture system, a six-dimensional force/torque sensor and a display.

The end of the collaborative robotic arm is fixedly connected with the six-dimensional force/torque sensor and a handle along the rotary axis, the reflective markers are fixedly pasted on the handle, and the handle is fixedly connected to an endpoint/joint of the limb when in use.

The optical motion capture system is configured to collect the three-dimensional position of the reflective markers and obtain the displacement/angle information of the subject's limb.

Reflective markers are configured to record limb posture.

The collaborative robotic arm is configured to construct a random small-perturbation motion environment in a three-dimensional space.

The six-dimensional force/torque sensor is configured to collect the measured force/torque information between the subject's limb and the end of the robotic arm.

The display provides the subject with visual feedback of real-time data from the six-dimensional force/torque sensor during dynamic interactions.

Preferably, the method for the restoring force/torque acquisition system to obtain the expression of the restoring force/torque with substituted time-varying impedance parameters includes the following steps:

According to the time-varying impedance characteristics of the subject's limb, the second-order impedance model is utilized to construct the time-varying dynamic system of the subject's limb.

By using the linear parameter varying method, the time-varying damping parameters of the subject's limbs and the time-varying stiffness parameters of the subject's limbs in the dynamic model are constructed as the weighted sum of functions with the scheduling variable as the independent variable, and the restoring force/torque is transformed to obtain the expression of the restoring force/torque with the substituted time-varying impedance parameters. The dynamic interaction force/torque is the scheduling variable.

Specifically, the method for the restoring force/torque acquisition system to obtain the expression of the restoring force/torque with substituted time-varying impedance parameters includes the following steps:

According to the time-varying impedance characteristics of the subject's limb, the second-order impedance model is used to construct the subject's limb time-varying dynamic system, and the expression thereof is:

$$I\ddot{x}(t)+B(t)\dot{x}(t)+K(t)x(t)=f_r(t)$$

In the expression, I is the inertial parameter of the subject's limb; B(t) is the time-varying damping parameter of the subject's limb; K(t) is the time-varying stiffness parameter of the subject's limb; x(t) is the displacement/angle of the subject's limb collected by the optical motion capture system; $f_r(t)$ is the restoring force/torque data of the subject's limb; $\dot{x}(t)$ is the first-order derivative of displacement/angle of the subject's limb; $\ddot{x}(t)$ is the second-order derivative of displacement/angle of the subject's limb; and t is time.

The linear parameter varying method is adopted to construct the time-varying damping parameter of the subject's limb and the time-varying stiffness parameter of the subject's limb in the dynamic model as the weighted sum of function with the scheduling variable dynamic interaction force/torque as the independent variable, and the expression thereof is:

$$K(t)=\sum_{i=0}^{P}a_i g_i(f_v(t)) \quad B(t)=\sum_{i=0}^{P}b_i g_i(f_v(t))$$

In the expression, B(t) is the time-varying damping parameter of the subject's limb, K(t) is the time-varying stiffness parameter of the subject's limb, $g_i(f_v(t))$ is the function with the dynamic interaction force/torque $f_v(t)$ as the independent variable, $a_i$ and $b_i$ are the weights of the i-th-order function, P is the maximum order of the function; and t is time.

The expression of the time-varying dynamics model of the subject's limb based on the expression with substituted time-varying impedance parameters is:

$$I\ddot{x}(t)+\sum_{i=0}^{P}b_i g_i(f_v(t))\dot{x}(t)+\sum_{i=0}^{P}a_i g_i(f_v(t))x(t)=f_r(t)$$

In the expression, I is the inertial parameter of the subject's limb, $g_i(f_v(t))$ is the function with dynamic interaction force/torque $f_v(t)$ as the independent variable, $a_i$ and $b_i$ are the weights of the i-th-order function, P is the maximum order of the function, $f_r(t)$ is the restoring force/torque of the subject's limb, x(t) is the displacement/angle of the subject's limb collected by the optical motion capture system, $\dot{x}(t)$ is the first-order derivative of the displacement/angle of the subject's limb, $\ddot{x}(t)$ is the second-order derivative of the displacement/angle of the subject's limb; and t is time.

The intermediate variables $x_g(i, t)$ and $\dot{x}_g(i, t)$ are constructed, and expressions are:

$$x_g(i,t)=g_i(f_v(t))x(t) \quad \dot{x}_g(i,t)=g_i(f_v(t))\dot{x}(t)$$

In the expressions, $x_g(i, t)$ is the intermediate variable constructed by the function $g_i(f_v(t))$ and the displacement/angle x(t) of the subject's limb, $g_i(f_v(t))$ is a function using dynamic interaction force/torque $f_v(t)$ as independent variable, $\dot{x}_g(i, t)$ is the intermediate variable constructed by the function $g_i(f_v(t))$ and the first-order derivative $\dot{x}(t)$ of the displacement/angle of the subject's limb, i is the order of the $g_i$ function, and t is time.

Based on the above expressions and variables that substitute time-varying impedance parameters, the expression of the reconstructed restoring force/torque is:

$$f_r(t)=\varphi(t)\beta\varphi(t)=[\ddot{x}(t)\dot{x}_g(0,t)x_g(1,t) \ldots \dot{x}_g(P,t)x_g(0,t)x_g(1,t) \ldots x_g(P,t)]\beta=[I\ b_0 b_1 \ldots b_p a_0 a_1 \ldots a_P]^T$$

In the expression, I is the inertial parameter of the subject's limb, $g_i(f_v(t))$ is the function with dynamic interaction force/torque $f_v(t)$ as the independent variable, $a_0 \ldots a_p$ and $b_0 \ldots b_p$ are the weights of the 0 ... P-th-order function, P is the maximum order of the function, $f_r(t)$ is the restoring force/torque of the subject's limb, x(t) is the displacement/angle of the subject's limb collected by the optical motion capture system, $\beta$ is a linear coefficient matrix composing of the inertial parameters I of the subject's limbs and the weights $a_0 \ldots a_p$ and $b_0 \ldots b_p$ of the 0 ... P-th-order function, $\varphi(t)$ is the displacement/angle parameter matrix consisting of the variables $x_g(i, t)$ and $\dot{x}_g(i, t)$, and the second-order derivative $\ddot{x}(t)$ of the displacement/angle of subject's limb, $x_g(i, t)$ is an intermediate variable constructed from the function $g_i(f_v(t))$ and the displacement/angle x(t) of the subject's limb, $\dot{x}_g(i, t)$ is an intermediate variable constructed from the function $g_i(f_v(t))$ and the first-order derivative $\dot{x}(t)$ of the displacement/angle of the subject's limb, i is the order of the $g_i$ function, and t is time.

Preferably, the method for the iterative parameter identification system to decouple the dynamic interaction force/torque and the restoring force/torque includes the following steps:

(1) The collected subject's limb displacement is combined with the measured force data or the angle is combined with the measured torque data, and initialize the estimated value of the initial restoring force/torque as 0.

(2) Based on the combination of subject's limb displacement and measured force data or the combination of angle and measured torque data, combined with the estimated value of restoring force/torque under the current iteration, and according to the fact that the measured force/torque is equal to the sum of restoring force/torque and dynamic interaction force/torque, the intermediate variable of dynamic interaction force/torque is obtained.

(3) According to the expression of the dynamic interaction force/torque expanded by the basis function, the intermediate variable of the dynamic interaction force/torque is utilized to identify the weights of the basis function.

(4) The estimated value of the dynamic interaction force/torque under the current iteration is obtained by using the weights of the basis function and the sequence of basis functions in the perturbation duration interval.

(5) According to the fact that the measured force/torque is equal to the sum of the restoring force/torque and the dynamic interaction force/torque, the intermediate variable of the restoring force/torque is obtained.

(6) Based on the expression of restoring force/torque with substituted time-varying impedance parameters, the intermediate variable of restoring force/torque is utilized to obtain a linear coefficient matrix.

(7) According to the displacement parameter matrix and the linear coefficient matrix obtained under the current iteration, the estimated value of the restoring force/torque under the current iteration is obtained.

(8) Return to step (2) until the actual number of iterations reaches the predetermined maximum number of iterations, and the linear coefficient matrix, the estimated value of restoring force/torque and the estimated value of dynamic interaction force/torque obtained in the last iteration are output.

Specifically, the expression of each step of the method for iterative identification to decouple dynamic interaction force/torque and restoring force/torque using time-varying dynamic parameters is:

Step: (1): Initialization is performed, $f_m(t)$, x(t), $\dot{x}(t)$ and $\ddot{x}(t)$ are known, and set the initial estimated value of $f_r(t)$ as $\hat{f}_r^{\ 0}(t)=0$.

Steps (2), (3), and (4): For the n-th iteration, the intermediate variable $\hat{f}_v^{\ temp}(t)=f_m(t)-\hat{f}_r^{\ n-1}(t)$ is calculated, and set $$\hat{f}_v^{\ temp}(t) = \sum_{j=0}^{Q} c_j h_j(t)$$

so as to identify the weight $c_j$, and the estimated value $\hat{f}_v^{\ n}(t)$ of obtained $f_v(t)$ is reconstructed.

Steps (5), (6), and (7): The intermediate variable $\hat{f}_r^{\ temp}(t)=f_m(t)-\hat{f}_v^{\ n}(t)$ is calculated, set $\hat{f}_r^{\ temp}(t)=\varphi(t)\beta$, so as to identify the parameter $\beta$, and the estimated value $\hat{f}_r^{\ n}(t)$ of obtained $f_r(t)$ is reconstructed.

Step (8): Set n=n+1, go back to step 2 until n exceeds the set maximum number of iterations, then the iteration is terminated.

In the expression, $f_m(t)$ is the measured force/torque, $f_v(t)$ is the dynamic interaction force/torque, $f_r(t)$ is the restoring force/torque, $\hat{f}_r^{\ 0}(t)$ is the initial value of the restoring force/torque, $\hat{f}_v^{\ temp}(t)$ is the intermediate variable, $\hat{f}_r^{\ n-1}(t)$ is the estimated value of the restoring force/torque in the n−1-th iteration, $\hat{f}_r^{\ temp}(t)$ is the intermediate variable, $\beta$ is the linear coefficient matrix composing of the inertial parameters I of the subject's limb, the weights $a_0 \ldots a_p$ and $b_0 \ldots b_p$ of the 0 ... P-th-order function, $\varphi(t)$ is the displacement parameter matrix composing of the variables $x_g(i, t)$ and $\dot{x}_g(i, t)$, and the second-order derivative $\ddot{x}(t)$ of the displacement/angle of the subject's limb, $\hat{f}_m^{\ n}(t)$ is the estimated value of measured force/torque of the n-th iteration, $\hat{f}_v^{\ n}(t)$ is the estimated value of the dynamic interaction force/torque of the n-th iteration, $\hat{f}_r^{\ n}(t)$ is the estimated value of the restoring force/torque of the n-th iteration; i and j are the order of the function, and t is time.

Preferably, the step for the dynamic interaction force/torque acquisition system to expand the basis function of dynamic interaction force/torque is as follows: the dynamic interaction force/torque is represented by the basis function sequence and the weights of the basis functions in the perturbation duration interval.

Specifically, the expression of dynamic interaction force/torque expanded by basis functions is:

$$f_v(t) = \sum_{j=0}^{Q} c_j h_j(t)$$

In the expression, $f_v(t)$ is the dynamic interaction force, $h_j(t)$ is the basis function sequence in the perturbation duration interval, $c_j$ represents the weight of the j-th-order basis function, Q is the maximum order of the basis function, and t is time.

In general, compared with the conventional technology, the above technical solutions conceived by the present disclosure have the following advantageous effects:

The dynamic interaction-oriented subject's limb time-varying stiffness identification method provided by the present disclosure is constructed based on the linear parameter varying method, the basis function expansion method and the iterative parameter identification method. The time-varying stiffness research problem of subject's limbs is transformed into a time-invariant research problem through the linear parameter varying method, thereby providing a new idea for the identification of time-varying stiffness. The provided iterative parameter identification can completely and accurately identify the time-varying stiffness of the subject's limbs by means of data in single perturbation, which significantly reduces complexity of the time-varying stiffness research. More importantly, the disclosure breaks through the limitation that the existing time-varying stiffness identification technology relying on single experimental data cannot be applied to the dynamic interaction with the environment. Generally speaking, the method for identifying the time-varying stiffness of a subject's limb provided by the present disclosure improves the accuracy of the time-varying stiffness identifying technique.

The motion data acquisition method for the time-varying stiffness identification of the subject's limb provided by the present disclosure can uniformly guide the experimental data acquisition of the time-varying stiffness research of the subject's limb. The experimental paradigm is simple, the operability is high, and the stiffness characteristics of the subject's limb can be completely changed. Moreover, the recorded data enables accurate resolution of the time-varying stiffness of the subject's limbs.

The present disclosure utilizes a multi-degree-of-freedom cooperative robotic arm to construct a small-perturbation environment to measure the time-varying stiffness of the subject's limb, thereby saving the complicated process of developing a special-purpose measuring device, reducing the difficulty of measuring the time-varying stiffness of the subject's limb, and expanding the application scenario of using the cooperative robotic arm for stiffness measurement, so that the time-varying stiffness measurement of the upper and lower limbs of the subject can be studied with the assistance of the cooperative robotic arm.

DESCRIPTION OF THE EMBODIMENTS

Figure 1:
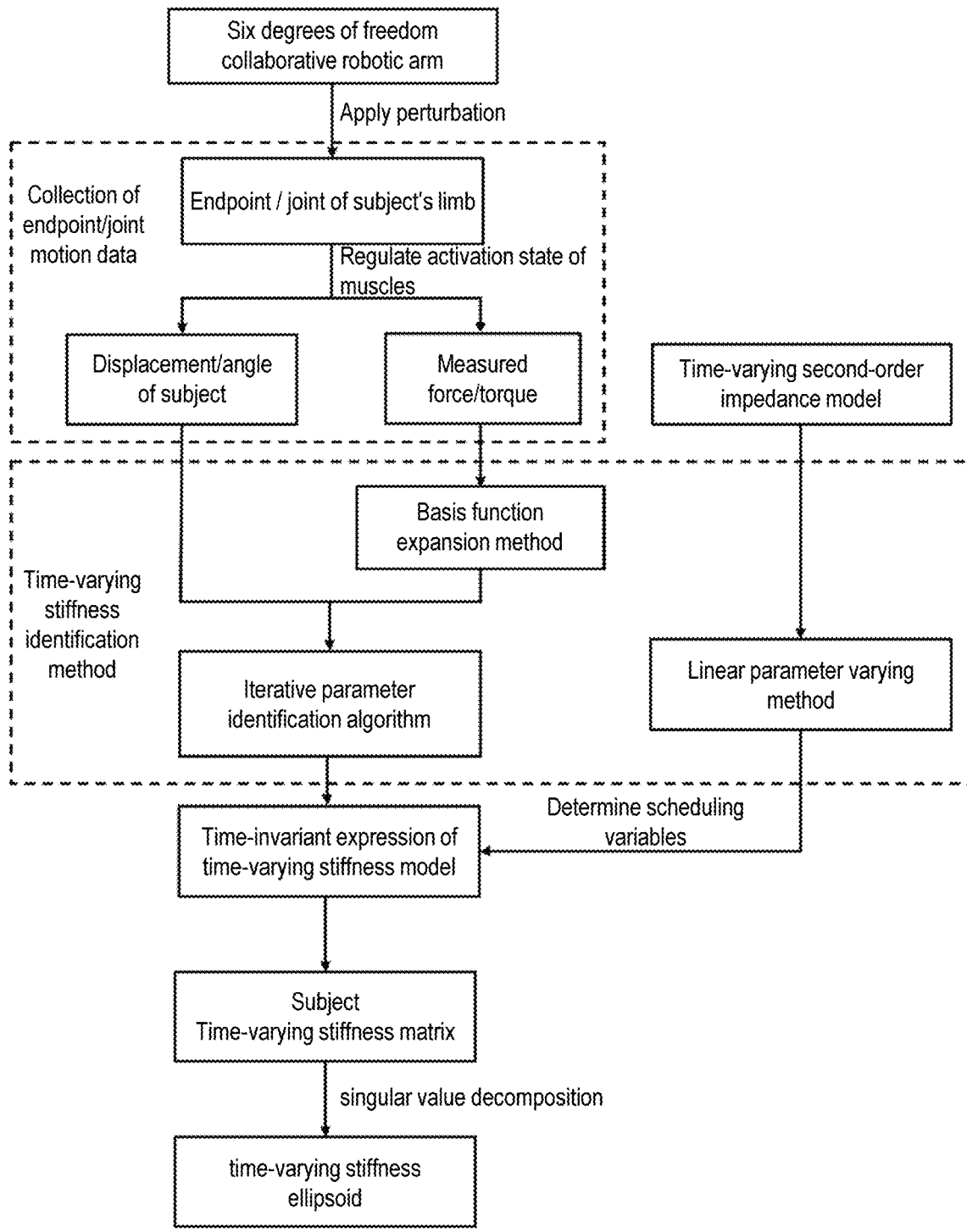
FIG. 1 is a schematic view of a dynamic interaction-oriented subject's limb time-varying stiffness identification method provided by an embodiment of the present disclosure.

In order to make the purpose, technical solutions and advantages of the present disclosure clearer, the present disclosure will be further described in detail below with reference to the accompanying drawings and embodiments. It should be understood that the specific embodiments described herein are only used to explain the present disclosure, but not to limit the present disclosure.

In one aspect, the present disclosure provides a dynamic interaction-oriented subject's limb time-varying stiffness identification method, including a motion data acquisition method and a time-varying stiffness identification method for subject's limb time-varying stiffness identification.

The process of motion data acquisition method for subject's limb time-varying stiffness identification is as follows: Under the random small-perturbation motion scenario constructed by the collaborative robotic arm, the impedance characteristics of the subject's limb is changed by adjusting the activation the states of muscles, and the physical sensors are used to obtain the subject's limb motion data.

The time-varying stiffness identification methods of subject's limb include linear parameter varying method, basis function expansion method and iterative identification method.

In the method, the linear parameter varying method converts the time-varying impedance parameters of the subject's limb into the form of time-invariant parameters, and then uses the basis function expansion method to describe the dynamic interaction force of the subject's limb. Thereafter, the iterative identification method is utilized to decouple the subject's limb restoring force and interaction force, and finally the accurate identification of the time-varying stiffness of the subject's limbs is achieved.

The time-varying stiffness identification method of the subject's limb provided by the present disclosure can not only obtain the time-varying stiffness of the limb endpoint, such as the upper limb endpoint, but also can calculate the time-varying stiffness of each joint of the subject's limb. In addition, the present disclosure is not limited to using the combination of dynamic interaction force and displacement data of the subject's limb to identify the stiffness of the subject's limb. When the database used for stiffness identification of the subject's limb is the combination of torque and angle data, the method provided by the present disclosure is also applicable, only that force is replaced with torque, and displacement is replaced with angle.

The Details are as Follows:

(1) Motion data collection for time-varying stiffness identification of subject's limb The disclosure uses the collaborative robotic arm to construct a three-dimensional spatial random perturbation motion environment. The subject's limb and the end of the collaborative robotic arm are firmly connected together. A certain number of reflective markers are fixed on the end of the collaborative robotic arm, and an optical motion capture system is used to collect the three-dimensional positions of the reflective markers to obtain the displacement/angle information of the subject's limb. A certain number of reflective markers will be fixed on the subject's limb and torso in order to record the limb posture.

The end of the robotic arm is connected with a six-dimensional force/torque sensor to collect the force/torque information between the subject's limb and the end of the robotic arm.

A computer monitor is placed directly in front of the subject to display the instantaneous force/torque of the six-dimensional force/torque sensor exerted by the subject limb on the end of the robotic arm during the experiment, providing visual feedback for the subject.

During the acquisition of the time-varying stiffness data of the subject's limbs, under the random small-perturbation motion environment established by the collaborative robotic arm, the limb end or joint of the subject are fixedly connected to the collaborative robotic arm, keeping the limb posture unchanged, and the time-varying stiffness of the subject's limb is adjusted by changing the states of the muscles.

The time-varying property of subject's limb stiffness is induced by the interaction force/torque recorded by the six-dimensional force/torque sensor at the end of the collaborative robotic arm. In each of the three directions (or rotation axes) of X, Y, and Z, the positive interaction force/torque is increased first and then decreased, and then the negative interaction force/torque is increased and then decreased. In this manner, when the interaction force/torque is changed in all the three directions (or rotation axis) a dynamic force/torque interaction cycle is completed.

Within the specified perturbation time, the subject's limb needs to complete at least one dynamic force/torque interaction cycle, and the completion time of each cycle is not limited.

The displacement/angle information and force/torque information of the subject's limb collected according to the above method can be used to identify the time-varying stiffness of the subject's limbs.

(2) Establishment of the time-varying dynamics model of the subject's limbs

In order to characterize the time-varying stiffness of subject's limbs, a second-order impedance model with a compact expression and capable of describing the time-varying characteristics of the subject's limb impedance is applied to model the subject's limb stiffness. The second-order impedance model is written as:

$$I\ddot{x}(t)+B(t)\dot{x}(t)+K(t)x(t)=f_r(t) \tag{1}$$

In the expression, I, B(t) and K(t) are collectively called impedance parameters, I is the inertial parameter of the subject's limb; B(t) is the time-varying damping parameter of the subject's limb; K(t) is the time-varying stiffness parameter of the subject's limb; x(t) is the displacement/angle of the subject's limb collected by the optical motion capture system; $f_r(t)$ is the restoring force/torque data of the subject's limb; $\dot{x}(t)$ is the first-order derivative of displacement/angle of the subject's limb; $\ddot{x}(t)$ is the second-order derivative of displacement/angle of the subject's limb. It can be seen from the above dynamic model that the displacement/angle x(t) and restoring force/torque $f_r(t)$ of the subject's limb under the small-perturbation environment are the key data for identifying the subject's limb stiffness. Specifically, the displacement/angle x(t) of the subject's limb is generally obtained by an optical motion capture system; the data recorded by the force/torque sensor on the end of the robotic arm during the interaction experiment is the measured force/torque $f_m(t)$ which consists of restoring force/torque $f_r(t)$ and interaction force/torque $f_v(t)$, and the relationship between the measured force/torque $f_m(t)$, the interaction force/torque $f_v(t)$, and the restoring force/torque $f_r(t)$ is expressed by:

$$f_m(t)=f_r(t)+f_v(t) \tag{2}$$

Therefore, decoupling the measured force/torque $f_m(t)$ to obtain the restoring force/torque $f_r(t)$ and dynamic interaction force/torque $f_v(t)$ of the subject's limb during the dynamic interaction is the key to obtain the time-varying stiffness identification of the subject's limb.

(3) Identification of time-varying stiffness of subject's limbs (3.1) Linear expression of time-varying impedance parameters of subject's limbs:

The idea of the linear parameter varying method is to determine some time-varying variables that directly affect the time-varying characteristics of the identified system through prior knowledge as scheduling variables, and then model the unknown time-varying impedance parameters as weighted sum of a series of functions of the scheduling variable. In dynamic interaction, the dynamic interaction force/torque $f_v(t)$ is the predominant variable reflecting the stiffness characteristics of the subject's limb. Therefore, the dynamic interaction force/torque $f_v(t)$ is set as the scheduling variable, the time-varying stiffness K(t) of the subject's limb and the time-varying damping B(t) of the subject's limb are constructed as weighted sum of a series of functions with the scheduling variable as the independent variable:

$$K(t) = \sum_{i=0}^{P} a_i g_i(f_v(t)) \quad B(t) = \sum_{i=0}^{P} b_i g_i(f_v(t)) \tag{3}$$

In the expression, B(t) is the time-varying damping parameter of the subject's limb, K(t) is the time-varying stiffness parameter of the subject's limb, $g_i(f_v(t))$ is the function with the dynamic interaction force/torque $f_v(t)$ as the independent variable, $a_i$ and $b_i$ are the weights of the i-th-order function, P is the maximum order of the function $g_i(f_v(t))$; and t is time.

By substituting formula (3) into formula (1), the following equation can be obtained:

$$I\ddot{x}(t) + \sum_{i=0}^{P} b_i g_i(f_v(t))\dot{x}(t) + \sum_{i=0}^{P} a_i g_i(f_v(t))x(t) = f_r(t) \tag{4}$$

In the expression, I is the inertial parameter of the subject's limb, $g_i(f_v(t))$ is the function with dynamic interaction force/torque $f_v(t)$ as the independent variable, $a_i$ and $b_i$ are the weights of the i-th-order function, P is the maximum order of the function, $f_r(t)$ is the restoring force/torque of the subject's limb, x(t) is the displacement/angle of the subject's limb collected by the optical motion capture system, $\dot{x}(t)$ is the first-order derivative of the displacement/angle of the subject's limb, $\ddot{x}(t)$ is the second-order derivative of the displacement/angle of the subject's limb; and t is time.

The variables $x_g(i, t)$ and $\dot{x}_g(i, t)$ are constructed as follows $$x_g(i,t)=g_i(f_v(t))x(t)\dot{x}_g(i,t)=g_i(f_v(t))\dot{x}(t) \tag{5}$$

In the expression, $g_i(f_v(t))$ is the function with dynamic interaction force/torque $f_v$ (t) as the independent variable, x(t) is the displacement/angle of the subject's limb collected by the optical motion capture system, ẋ(t) is the first-order derivative of the displacement/angle of the subject's limb, i is the order of the function $g_i(f_v(t))$, and t is time.

The formula (4) can be transformed into the following form:

$$f_r(t)=\varphi(t)\beta\varphi(t)=[\ddot{x}(t)\dot{x}_g(0,t)\dot{x}_g(1,t) \ldots \dot{x}_g(P,t)x_g(0,t)x_g(1,t) \ldots x_g(P,t)]\beta=[I\ b_0b_1 \ldots b_Pa_0a_1 \ldots a_P]^T \quad (6)$$

In the expression, I is the inertial parameter of the subject's limb, $g_i(f_v(t))$ is the function with dynamic interaction force/torque $f_v(t)$ as the independent variable, $a_0 \ldots a_p$ and $b_0 \ldots b_p$ are the weights of the 0 ... P-th-order function, P is the maximum order of the function $g_i(f_v(t))$, $f_r(t)$ is the restoring force/torque of the subject's limb, x(t) is the displacement of the subject's limb collected by the optical motion capture system, β is a linear coefficient matrix composing of the inertial parameters I of the subject's limbs and the weights $a_0 \ldots a_p$ and $b_0 \ldots b_p$ of the 0 ... P-th-order function, φ(t) is the displacement/angle parameter matrix consisting of the variables $x_g(i, t)$, $\dot{x}_g(i, t)$, and the second-order derivative ẍ(t) of the displacement/angle of subject's limb, $x_g(i, t)$ is an intermediate variable constructed through $g_i(f_v(t))$, x(t), $\dot{x}_g(i, t)$ is an intermediate variable constructed through $g_i(f_v(t))$ and ẋ(t), i is the order of the function $g_i(f_v(t))$, and t is time.

Through the above process, the identification problem of time-varying parameters is transformed into the identification problem of time-invariant parameters through linear parameter varying method.

(3.2) Basis function expansion of dynamic interaction force/torque $f_v(t)$:

In order to construct the time-invariant expression of the dynamic interaction force/torque $f_v(t)$, the basis function expansion method is utilized to express the dynamic interaction force. The basis function expansion used for modeling the dynamic interaction force/torque $f_v(t)$ is as follows:

$$f_v(t) = \sum_{j=0}^{Q} c_j h_j(t) \quad (7)$$

In the expression, $f_v(t)$ is the dynamic interaction force, $h_j(t)$ is the basis function sequence in the perturbation duration interval, $c_j$ represents the weight of the j-th-order basis function, Q is the maximum order of the basis function; and t is time.

Since the basis function $h_j(t)$ is only related to time, when the structure and order of the basis function are determined, the weight value $c_0, c_j, \ldots, c_Q$ can be obtained by means of the linear regression method.

(3.3) Iterative identification of parameters for time-varying dynamic systems

Based on the above description of the dynamic interaction force/torque $f_v(t)$ and the restoring force/torque $f_r(t)$ of the subject's limb, these two forces are decoupled from the measured force/torque data $f_m(t)$ through a step-by-step iterative identification method. The steps of the iterative identification method are as follows:

1: Initialization is performed, $f_m(t)$, x(t), ẋ(t) and ẍ(t) are known, and let the initial estimated value of $f_r(t)$ as $\hat{f}_r^0(t)=0$.

2: For the n-th iteration, the intermediate variable $\hat{f}_v^{temp}(t)=f_m(t)-\hat{f}_r^{n-1}(t)$ is calculated, and let $$\hat{f}_v^{temp}(t) = \sum_{j=0}^{Q} c_j h_j(t)$$

according to formula (7), so as to identify the weight $c_j$, and then the estimated value $\hat{f}_v^n(t)$ of $f_v(t)$ is obtained through formula (7).

3: The intermediate variable $\hat{f}_r^{temp}(t)=f_m(t)=f_m(t)-\hat{f}_v^n(t)$ is calculated, according to formula (5) and formula (6), let $\hat{f}_r^{temp}(t)=\varphi(t)\beta$, so as to identify the parameter β, and the estimated value $\hat{f}_r^n(t)$ of $f_r(t)$ is obtained through formula (6).

4: Let n=n+1, go back to step 2 until n exceeds the predefined maximum iteration number, then the iteration is terminated.

In the expression, $f_m(t)$ is the measured force/torque, $f_v(t)$ is the dynamic interaction force/torque, $f_r(t)$ is the restoring force/torque, $\hat{f}_r^0(t)$ is the initial value of the restoring force/torque, $\hat{f}_v^{temp}(t)$ is the intermediate variable, $\hat{f}_r^{n-1}(t)$ is the estimated value of the restoring force/torque in the n−1-th iteration, $\hat{f}_r^{temp}(t)$ is the intermediate variable, β is the matrix composing of the inertial parameter I of the subject's limb, the weights $a_0 \ldots a_p$ and $b_0 \ldots b_p$ of the 0 ... P-th-order function, φ(t) is the matrix composing of the variables $x_g(i, t)$ and $\dot{x}_g(i, t)$, and the second-order derivative ẍ(t) of the displacement/angle of the subject's limb, $\hat{f}_m^n(t)$ is the estimated value of measured force/torque after the n-th iteration, $\hat{f}_v^n(t)$ is the estimated value of the dynamic interaction force/torque after the n-th iteration, $\hat{f}_r^n(t)$ is the estimated value of the restoring force/torque after the n-th iteration; i and j are the order of the corresponding functions, and t is time.

After the above iterative identification algorithms are performed, the weight values in formula (3) can be extracted from the parameter β, and the weight value and the value of the dynamic interaction force are substituted into formula (3) to obtain the time-varying stiffness K(t) of the subject's limb during the dynamic interaction process.

The present disclosure also provides a dynamic interaction-oriented subject's limb time-varying stiffness identification device, including: a data acquisition system, a restoring force/torque acquisition system, an iterative parameter identification system, and a dynamic interaction force/torque acquisition system.

(1) The Data Acquisition System

The data acquisition system is configured to collect the combination of the subject's limb displacement and measured force data or the combination of angle and measured torque data under the random small-perturbation motion environment where the subject changes the muscle contraction level but keeps the limb posture fixed, so as to construct a database for time-varying stiffness identification of subject's limbs.

The data acquisition system includes a collaborative robotic arm, reflective markers, an optical motion capture system, a six-dimensional force/torque sensor and a computer monitor.

The end of the collaborative robotic arm is fixedly connected with the six-dimensional force/torque sensor and a handle along the rotary axis, the reflective markers are fixedly pasted on the handle, and the handle is fixedly connected to an endpoint/joint of the limb when in use.

The optical motion capture system is configured to collect the three-dimensional position of the reflective markers and obtain the displacement/angle information of the subject's limb.

Reflective markers are configured to record limb posture.

The collaborative robotic arm is configured to construct a random small-perturbation motion environment in a three-dimensional space.

The six-dimensional force/torque sensor is configured to collect the measured force/torque information between the subject's limb and the end of the robotic arm.

The display provides the subject with visual feedback of real-time data from the six-dimensional force/torque sensor during dynamic interactions.

(2) The Restoring Force/Torque Acquisition System

The restoring force/torque acquisition system is configured to construct the expression of restoring force/torque with substituted time-varying impedance parameter of the subject's limb by using the linear parameter varying method.

The method for the restoring force/torque acquisition system to obtain the expression of the restoring force/torque with substituted time-varying impedance parameters includes the following steps:

According to the time-varying impedance characteristics of the subject's limb, the second-order impedance model is utilized to construct the time-varying dynamic model of the subject's limb.

By using the linear parameter varying method, the time-varying damping parameters of the subject's limbs and the time-varying stiffness parameters of the subject's limbs in the dynamic model are constructed as the weighted sum of functions with the scheduling variable as the independent variable, and the restoring force/torque is transformed to obtain the expression of the restoring force/torque with the substituted time-varying impedance parameters. The dynamic interaction force/torque is the scheduling variable.

Specifically, the method for the restoring force/torque acquisition system to obtain the expression of the restoring force/torque with substituted time-varying parameters includes the following steps:

According to the time-varying impedance characteristics of the subject's limb, the second-order impedance model is used to construct the subject's limb time-varying dynamics, and its expression is:

$$I\ddot{x}(t)+B(t)\dot{x}(t)+K(t)x(t)=f_r(t)$$

In the expression, t is time, I is the inertial parameter of the subject's limb; B(t) is the time-varying damping parameter of the subject's limb; K(t) is the time-varying stiffness parameter of the subject's limb; x(t) is the displacement/angle of the subject's limb collected by the optical motion capture system; $f_r(t)$ is the restoring force/torque data of the subject's limb; $\dot{x}(t)$ is the first-order derivative of displacement/angle of the subject's limb; and $\ddot{x}(t)$ is the second-order derivative of displacement/angle of the subject's limb.

The linear parameter varying method is adopted to construct the time-varying damping parameter of the subject's limb and the time-varying stiffness parameter of the subject's limb in the dynamic model as the weighted sum of function with the scheduling variable dynamic interaction force/torque, as the independent variable, and its expression is:

$$K(t) = \sum_{i=0}^{P} a_i g_i(f_v(t)) B(t) = \sum_{i=0}^{P} b_i g_i(f_v(t))$$

In the expression, B(t) is the time-varying damping parameter of the subject's limb, K(t) is the time-varying stiffness parameter of the subject's limb, $g_i(f_v(t))$ is the function with the dynamic interaction force/torque $f_v(t)$ as the independent variable, $a_i$ and $b_i$ are the weights of the i-th-order function $g_i$, P is the maximum order of the function; and t is time.

After substituting the time-varying impedance parameters as above, the time-varying dynamics model of the subject's limb is expressed as:

$$I\ddot{x}(t) + \sum_{i=0}^{P} b_i g_i(f_v(t))\dot{x}(t) + \sum_{i=0}^{P} a_i g_i(f_v(t))x(t) = f_r(t)$$

In the expression, t is time; I is the inertial parameter of the subject's limb, $g_i(f_v(t))$ is the function with dynamic interaction force/torque $f_v(t)$ as the independent variable, $a_i$ and $b_i$ are the weights of the i-th-order function $g_i$, P is the maximum order of the function, $f_r(t)$ is the restoring force/torque of the subject's limb, x(t) is the displacement/angle of the subject's limb collected by the optical motion capture system, $\dot{x}(t)$ is the first-order derivative of the displacement/angle of the subject's limb, and $\ddot{x}(t)$ is the second-order derivative of the displacement/angle of the subject's limb.

The intermediate variables $x_g(i, t)$ and $\dot{x}_g(i, t)$ are constructed with expressions as below:

$$x_g(i,t)=g_i(f_v(t))x(t) \quad \dot{x}_g(i,t)=g_i(f_v(t))\dot{x}(t)$$

In the expressions, $x_g(i, t)$ is the intermediate variable constructed by the function $g_i(f_v(t))$ and the displacement/angle x(t) of the subject's limb, $\dot{x}_g(i, t)$ is the intermediate variable constructed by the function $g_i(f_v(t))$ and the first-order derivative $\dot{x}(t)$ of the displacement/angle of the subject's limb, i is the order of the $g_i$ function, and t is time.

Based on the above variables and expressions substituted by time-varying impedance parameters, the restoring force/torque can be written as:

$$f_r(t)=\varphi(t)\beta\varphi(t)=[\ddot{x}(t)\dot{x}_g(0,t)\dot{x}_g(1,t) \ldots \dot{x}_g(P,t)x_g(0,t)x_g(1,t) \ldots x_g(P,t)]\beta=[I\ b_0 b_1 \ldots b_P a_0 a_1 \ldots a_P]^T$$

In the expression, I is the inertial parameter of the subject's limb, $g_i(f_v(t))$ is the function with dynamic interaction force/torque $f_v(t)$ as the independent variable, $a_0 \ldots a_p$ and $b_0 \ldots b_p$ are the weights of the 0 . . . P-th-order function, P is the maximum order of the function, $f_r(t)$ is the restoring force/torque of the subject's limb, x(t) is the displacement/angle of the subject's limb collected by the optical motion capture system, β is a linear coefficient matrix composing of the inertial parameter I of the subject's limbs and the weights $a_0 \ldots a_p$ and $b_0 \ldots b_p$ of the 0 . . . P-th-order function, $\varphi(t)$ is the displacement/angle parameter matrix consisting of the intermediate variables $x_g(i, t)$, $\dot{x}_g(i, t)$, and the second-order derivative $\ddot{x}(t)$ of the displacement/angle of the subject's limb, $x_g(i, t)$ is an intermediate variable constructed from the function $g_i(f_v(t))$ and the displacement/angle x(t) of the subject's limb, $\dot{x}_g(i, t)$ is an intermediate variable constructed from the function $g_i(f_v(t))$ and the first-order derivative $\dot{x}(t)$ of the displacement/angle of the subject's limb, i is the order of the $g_i$ function, and t is time.

(3) The Iterative Parameter Identification System

The iterative parameter identification system is configured to, based on the expression of restoring force/torque with substituted time-varying impedance parameters and the expression of dynamic interaction force/torque expanded by basis functions, and according to the combination of the subject's limb displacement and measured force data or the combination of angle and measured torque data, perform iterative identification to decouple dynamic interaction force/torque and restoring force/torque by using parameters of time-varying dynamics.

The method for the iterative parameter identification system to decouple the dynamic interaction force/torque and the restoring force/torque includes the following steps:

(1) The collected subject's limb displacement is combined with the measured force data or the angle is combined with the measured torque data, and initialize the estimated value of the initial restoring force/torque as 0.

(2) Based on the combination of subject's limb displacement and measured force data or the combination of angle and measured torque data, and the estimated restoring force/torque under the current iteration, according to the fact that the measured force/torque is equal to the sum of restoring force/torque and dynamic interaction force/torque, the intermediate variable of dynamic interaction force/torque is obtained.

(3) According to the expression of the dynamic interaction force/torque expanded by the basis function, the intermediate variable of the dynamic interaction force/torque is utilized to identify the weights of the basis function.

(4) The estimate of the dynamic interaction force/torque under the current iteration is obtained by using the weights of the basis function and the sequence of basis functions in the perturbation duration interval.

(5) According to the fact that the measured force/torque is equal to the sum of the restoring force/torque and the dynamic interaction force/torque, the intermediate variable of the restoring force/torque is obtained.

(6) Based on the expression of restoring force/torque with substituted time-varying impedance parameters, the intermediate variable of restoring force/torque is utilized to obtain a linear coefficient matrix.

(7) According to the displacement parameter matrix and the linear coefficient matrix obtained under the current iteration, the estimate of the restoring force/torque under the current iteration is obtained.

(8) Return to step (2) until the actual number of iterations reaches the predetermined maximum number of iterations, and the linear coefficient matrix, the estimated restoring force/torque and the estimated dynamic interaction force/torque obtained in the last iteration are output.

Specifically, the iterative parameter identification system consists of the following steps:

Step: (1): Initialization is performed, $f_m(t)$, $x(t)$, $\dot{x}(t)$ and $\ddot{x}(t)$ are given, and set the initial estimate of $f_r(t)$ as $\hat{f}_r^0(t)=0$.

Steps (2), (3), and (4): For the n-th iteration, the intermediate variable $\hat{f}_v^{temp}(t)=f_m(t)-\hat{f}_r^{n-1}(t)$ is calculated, and set $$\hat{f}_v^{temp}(t) = \sum_{j=0}^{Q} c_j h_j(t),$$

so as to identify the weight $c_j$, and the estimated value $\hat{f}_v^n(t)$ of obtained $f_v(t)$ is reconstructed.

Steps (5), (6), and (7): The intermediate variable $\hat{f}_r^{temp}(t)=f_m(t)-\hat{f}_v^n(t)$ is calculated, set $\hat{f}_r^{temp}(t)=\varphi(t)\beta$, so as to identify the parameter $\beta$, and the estimated value $\hat{f}_r^n(t)$ of obtained $f_r(t)$ is reconstructed.

Step (8): Set n=n+1, go back to step 2 until n exceeds the set maximum number of iterations, then the iteration is terminated.

In the expression, $f_m(t)$ is the measured force/torque, $f_v(t)$ is the dynamic interaction force/torque, $f_r(t)$ is the restoring force/torque, $\hat{f}_r^0(t)$ is the initial value of the restoring force/torque, $\hat{f}_v^{temp}(t)$ is the intermediate variable, $\hat{f}_r^{n-1}(t)$ is the estimated value of the restoring force/torque in the n−1-th iteration, $\hat{f}_r^{temp}(t)$ is the intermediate variable, β is the linear coefficient matrix composing of the inertial parameter $I_{end}$ of the subject's limb, the weights $a_0 \ldots a_p$ and $b_0 \ldots b_p$ of the $0 \ldots$ P-th-order function, $\varphi(t)$ is the displacement parameter matrix composing of the variables $x_g(i, t)$ and $\dot{x}_g(i, t)$, and the second-order derivative $\ddot{x}(t)$ of the displacement/angle of the subject's limb, $\hat{f}_n^m(t)$ is the estimated value of measured force/torque of the n-th iteration, $\hat{f}_v^n(t)$ is the estimated value of the dynamic interaction force/torque of the n-th iteration, $\hat{f}_r^n(t)$ is the estimated value of the restoring force/torque of the n-th iteration; i and j are the order of the function, and t is time.

(4) The dynamic interaction force/torque acquisition system

The dynamic interaction force/torque acquisition system is configured to expand the dynamic interaction force/torque using the basis function, and the dynamic interaction force/torque is represented by the basis function sequence in the perturbation duration interval and the weights of the basis function.

The step for the dynamic interaction force/torque acquisition system to expand the basis function of dynamic interaction force/torque is as follows: the dynamic interaction force/torque is represented by the basis function sequence and the weights of the basis functions in the perturbation duration interval.

Specifically, the expression of dynamic interaction force/torque expanded by basis functions is:

$$f_v(t) = \sum_{j=0}^{Q} c_j h_j(t)$$

In the expression, $f_v(t)$ is the dynamic interaction force, $h_j(t)$ is the basis function sequence in the perturbation duration interval, $c_j$ represents the weight of the j-th-order basis function, Q is the maximum order of the basis function, and t is time.

EMBODIMENT

In this embodiment, a six degrees of freedom collaborative robotic arm is used to apply a three-dimensional random perturbation to the end of the upper limbs of the human body, thereby constructing a motion scene of random small-perturbation. The stiffness characteristics of the end of upper limbs are changed by changing the activation state of the muscles, the displacement and restoring force data of the end of upper limbs are collected by physical sensors in the perturbation process, and the three-dimensional time-varying stiffness of the end of upper limbs is calculated according to the provided time-varying stiffness identification method. The overall measurement process is shown in FIG. 1, which includes the following steps:

(1) Collection of motion data of the end of upper limbs

Figure 2:
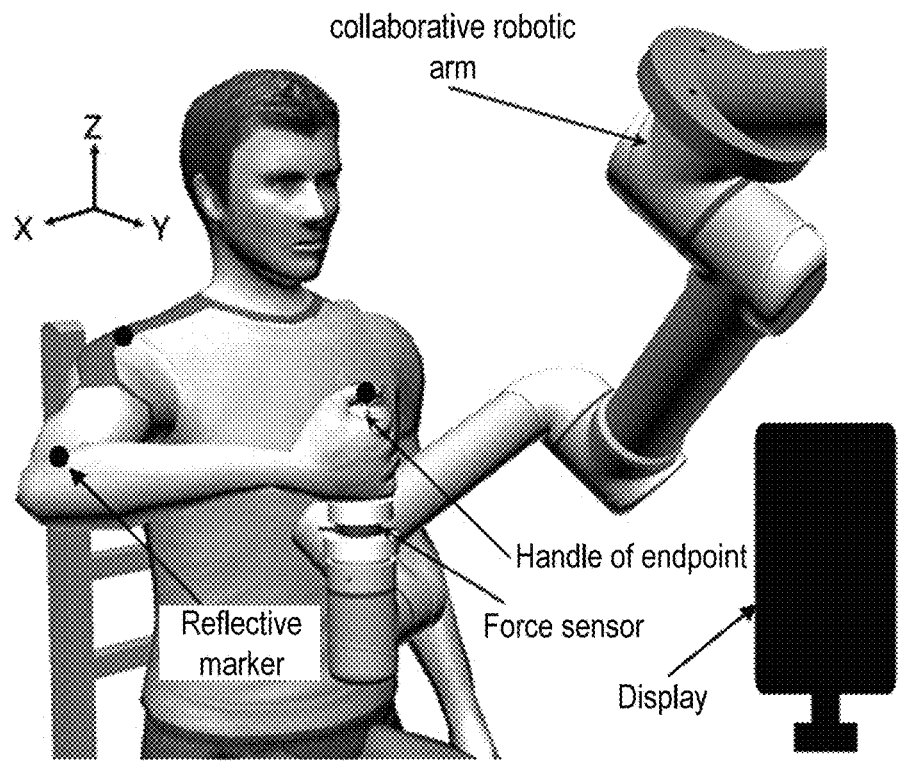
FIG. 2 is a schematic view of a perturbation test provided by an embodiment of the present disclosure.
Figure 3:
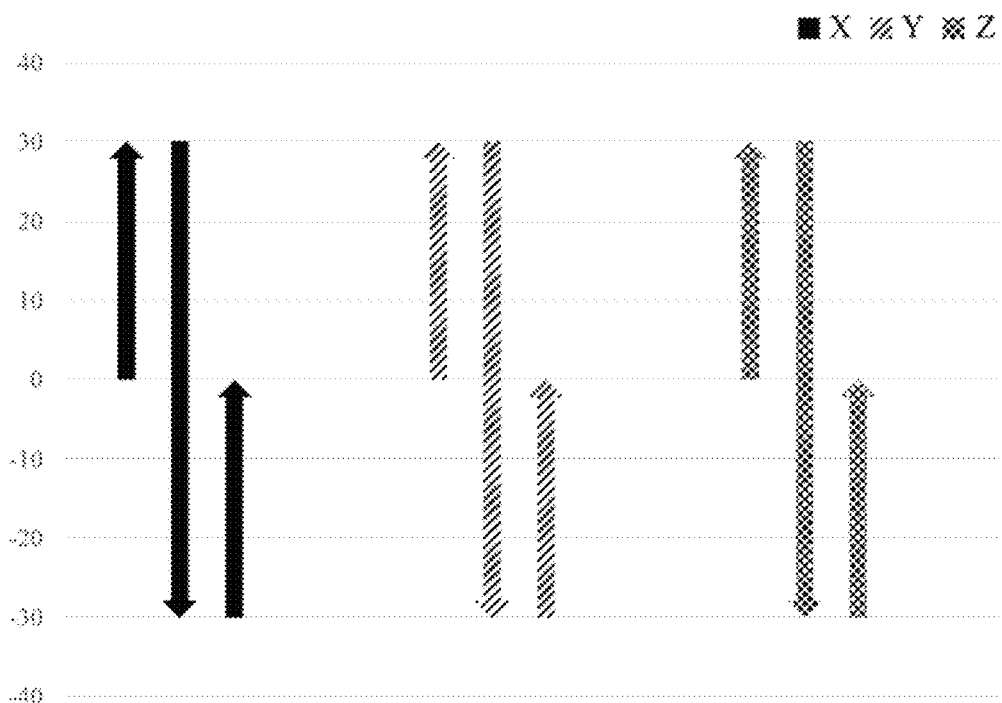
FIG. 3 is a force cycle change diagram in the experiment process provided by an embodiment of the present disclosure.

The subject sat on a hard chair, and the handle of the six degrees of freedom collaborative robotic arm was located 390 mm in front of and 100 mm below the rotation midline of the subject's right shoulder, as shown in FIG. 2. After the subject held the handle fixed on the end of the robotic arm, the machinery was activated and the robotic arm performed perturbation. The maximum amplitude of perturbation was set to 10 mm, and the frequency range was set to 0-5 Hz. The setting of parameters may ensure that the perturbation process provides accurate data for the subsequent kinetic identification of ends. The subject's upper limbs maintained a fixed posture, and the activation state of the muscles was adjusted to change the stiffness characteristics of the end of limbs. The force sensor fixed at the end of the robotic arm collected the data of the restoring force and dynamic interaction force generated by the upper limb due to the perturbation. The external optical 3D motion capture system collected displacement data of the end of limbs. During the process of motion data collection, a monitor was placed in front of the subject to display the force/torque change of the six-dimensional force/torque sensor on the end of the robotic arm during the experiment, providing visual feedback for the subject. The subject needed to perform a force cycle with a range of ±30 N in the three directions of X, Y and Z respectively. According to the force feedback information provided by the display, the positive interaction force was first increased and then decreased, and then the negative interaction force was increased then reduced, and the force cycle in three directions was completed in the manner described above, which is a dynamic force interaction cycle. During the perturbation duration interval of 20 seconds, the subject needed to complete at least one cycle of dynamic force transformation, and the completion time of each cycle is not limited. The force cycle of the measured force is shown in FIG. 3.

(2) Establishment of the time-varying dynamics model of the end of upper limbs

In order to characterize the time-varying stiffness characteristics of the end of upper limbs of human body, a second-order impedance model with a simple structure and capable of more comprehensively reflecting the time-varying impedance characteristics of the end of upper limbs of human body is applied to the research of the stiffness identification of the end of upper limbs. The dynamic model of the second-order impedance model is typically modeled as:

$$I\ddot{x}(t)+B(t)\dot{x}(t)+K(t)x(t)=f_r(t) \quad (1)$$

In the expression, t is time, I is the inertial parameter of the end of upper limbs of human body; B(t) is the time-varying damping parameter of the end of upper limbs of human body; K(t) is the time-varying stiffness parameter of the end of upper limbs of human body; x(t) is the displacement of the end of upper limbs of human body collected by the optical motion capture system; $f_r(t)$ is the restoring force/torque data of the end of upper limbs of human body; $\dot{x}(t)$ is the first-order derivative of displacement of the end of upper limbs of human body; and $\ddot{x}(t)$ is the second-order derivative of displacement of the end of upper limbs of human body. It can be seen from the above dynamic model that the displacement x(t) of the end of upper limbs of human body and restoring force $f_r(t)$ of the end of upper limbs under the small-perturbation environment are the key data for identifying the stiffness of the end. Specifically, the displacement x(t) of the end of upper limbs of human body is generally obtained by an optical motion capture system; the restoring force $f_r(t)$ of the end of upper limbs is part of the data recorded by the force/torque sensor on the end of the robotic arm. The data recorded by the force/torque sensor on the end of the robotic arm during the dynamic interaction process is the measured force $f_m(t)$, and the relationship between the measured force $f_m(t)$, the dynamic interaction force $f_v(t)$, and the restoring force $f_r(t)$ is expressed as:

$$f_m(t)=f_r(t)+f_v(t) \quad (2)$$

Therefore, decoupling the measured force $f_m(t)$ to obtain the restoring force $f_r(t)$ and dynamic interaction force $f_v(t)$ of the end of upper limbs of human body during the dynamic interaction process is the key to solving the time-varying stiffness identification of the end of upper limbs of human body.

(3) Calculation of time-varying stiffness of end of upper limbs of human body (3.1) Linear expression of time-varying impedance parameters of end of upper limbs of human body The idea of the linear parameter varying method is to determine some time variables that directly affect the time-varying characteristics of the system in the identified system through prior knowledge as scheduling variables, and then model the unknown time-varying parameters as weighted sum of a series of functions of scheduling variables. In the dynamic interaction process, it is difficult to directly obtain the active state of all muscles of the subject's upper limbs, but the joint action of subject's upper limbs allows the end of subject's upper limbs and the external environment to exhibit the dynamic interaction force $f_v(t)$, and therefore the dynamic interaction force $f_v(t)$ directly affects the stiffness characteristics of the system. Based on the above analysis, the dynamic interaction force $f_v(t)$ may be set as the scheduling variable. After the scheduling variable is determined, the time-varying stiffness $K_{end}$ (t) of the end of subject's upper limbs and the time-varying damping $B_{end}$ (t) of the end of subject's upper limbs are constructed as weighted sum of a series of functions with the scheduling variable as the independent variable:

$$K(t) = \sum_{i=0}^{P}a_ig_i(f_v(t))B(t) = \sum_{i=0}^{P}b_ig_i(f_v(t)) \quad (3)$$

In the expression, B(t) is the time-varying damping parameter of the end of upper limbs of human body, K(t) is the time-varying stiffness parameter of the end of upper limbs of human body, $g_i(f_v(t))$ is the function with the dynamic interaction force $f_v(t)$ as the independent variable, $a_i$ and $b_i$ are the weights of the i-th-order function, P is the maximum order of the function; and t is time.

By substituting formula (3) into formula (1), the following may be obtained:

$$I_{end}\ddot{x}(t) + \sum_{i=0}^{P}b_ig_i(f_v(t))\dot{x}(t) + \sum_{i=0}^{P}a_ig_i(f_v(t))x(t) = f_r(t) \quad (4)$$

In the expression, $I_{end}$ is the inertial parameter of the end of upper limbs of human body, $g_i(f_v(t))$ is the function with dynamic interaction force $f_v(t)$ as the independent variable, $a_i$ and $b_i$ are the weights of the i-th-order function, P is the maximum order of the function, $f_r(t)$ is the restoring force of the end of upper limbs of human body, x(t) is the displacement of the end of upper limbs of human body collected by the optical motion capture system, $\dot{x}(t)$ is the first-order derivative of the displacement of the end of upper limbs of human body, $\ddot{x}(t)$ is the second-order derivative of the displacement of end of upper limbs of human body; and t is time.

The variables $x_g(i, t)$ and $\dot{x}_g(i, t)$ are constructed, and set $$x_g(i,t)=g_i(f_v(t))x(t)\dot{x}_g(i,t)=g_i(f_v(t))\dot{x}(t) \quad (5)$$

The formula (4) may be transformed into the following form:

$$f_r(t)=\varphi(t)\beta\varphi(t)=[\ddot{x}(t)\dot{x}_g(0,t)\dot{x}_g(1,t) \ldots \dot{x}_g(P,t)x_g(0,t)x_g(1,t) \ldots x_g(P,t)]\beta=[I\ b_0 b_1 \ldots b_P a_0 a_1 \ldots a_P]^T$$

In the expression, $I_{end}$ is the inertial parameter of the human body, $g_i(f_v(t))$ is the function with dynamic interaction force $f_v(t)$ as the independent variable, $a_0 \ldots a_p$ and $b_0 \ldots b_p$ are the weights of the $0 \ldots$ P-th-order function, P is the maximum order of the function, $f_r(t)$ is the restoring force of the human body, $x(t)$ is the displacement of the human body collected by the optical motion capture system, $\beta$ is a linear coefficient matrix composing of the inertial parameters I of the human body and the weights $a_0 \ldots a_p$ and $b_0 \ldots b_p$ of the $0 \ldots$ P-th-order function, $\varphi(t)$ is the displacement parameter matrix consisting of the variables $x_g(i, t)$ and $\dot{x}g(i, t)$, and the second-order derivative $\ddot{x}(t)$ of the displacement of human body, $x_g(i, t)$ is an intermediate variable constructed through $g_i(f_v(t))$ and $x(t)$, $\dot{x}_g(i, t)$ is an intermediate variable constructed through $g_i(f_v(t))$ and $\dot{x}(t)$, i is the order of the $g_i$ function, and t is time.

Through the above process, the linear parameter varying method transforms the problem of time-varying system parameters identification into the problem of time-invariant unknown parameters identification. This embodiment chooses to use the 0-3rd order Chebyshev polynomial as the function $g_i(f_v(t))$ describing the relationship between the time-varying impedance parameters of the end of upper limb and the dynamic interaction force, but the form of the function $g_i(f_v(t))$ is not limited to the Chebyshev polynomial.

(3.2) Basis function expansion of dynamic interaction force $f_v(t)$:

In order to construct the time-invariant expression of the dynamic interaction force $f_v(t)$, the basis function expansion method is utilized to express the dynamic interaction force.

The basis function expansion for the dynamic interaction force $f_v(t)$ is as follows:

$$f_v(t) = \sum_{j=0}^{Q} c_j h_j(t) \quad (7)$$

In the expression, $f_v(t)$ is the dynamic interaction force, $h_j(t)$ is the basis function sequence in the perturbation duration interval, $c_j$ represents the weight of the j-th-order basis function, Q is the maximum order of the basis function; and t is time. Since the dynamic interaction force is characterized in smoothness, the B-spline basis function is selected as the basis function $h_j(t)$ because of being able to well describe the amount of smooth change. Based on the requirement for the identification accuracy of dynamic interaction force, it is necessary to use a basis function with higher order. However, if the order is too high, it is likely to cause an increase in the number of unknown parameters and reduce the overall identification result. In this embodiment, the maximum order of the B-spline basis function is set to 30, and this order setting may substantially ensure that the overall variation regularity of the described variable and the subtle variation in some time intervals may be well estimated.

(3.3) Iterative identification for parameters of time-varying dynamic system for end of upper limbs Based on the above description of the dynamic interaction force $f_v(t)$ and the restoring force $f_r(t)$ of human body, the two parts of the force are decoupled from the measured force data $f_m(t)$ through a step-by-step iterative identification method. The steps of the iterative identification method are as follows:

1: Initialization is performed, $f_m(t)$, $x(t)$, $\dot{x}(t)$ and $\ddot{x}(t)$ are known, and set the initial estimated value of $f_r(t)$ as $\hat{f}_r^0(t)=0$.

2: For the n-th iteration, the intermediate variable $\hat{f}_v^{temp}(t)=f_m(t)-\hat{f}_r^{n-1}(t)$ is calculated, and set $$\hat{f}_v^{temp}(t) = \sum_{j=0}^{Q} c_j h_j(t)$$

according to formula (7), so as to identify the weight $c_j$, and the estimated value $\hat{f}_v^n(t)$ of obtained $f_v(t)$ is reconstructed.

3: The intermediate variable $\hat{f}_r^{temp}(t)=f_m(t)-\hat{f}_v^n(t)$ is calculated, according to formula (5) and formula (6), set $\hat{f}_r^{temp}(t)=\varphi(t)\beta$, so as to identify the parameter $\beta$, and the estimated value $\hat{f}_r^n(t)$ of obtained $f_r(t)$ is reconstructed.

4: Set n=n+1, go back to step 2 until n exceeds the set maximum number of iterations, then the iteration is terminated.

In the expression, $f_m(t)$ is the measured force, $f_v(t)$ is the dynamic interaction force, $f_r(t)$ is the restoring force, $\hat{f}_r^0(t)$ is the initial value of the restoring force, $\hat{f}_v^{temp}(t)$ is the intermediate variable, $\hat{f}_r^{n-1}(t)$ is the estimated value of the restoring force in the n-1-th iteration, $\hat{f}_r^{temp}(t)$ is the intermediate variable, $\beta$ is the matrix composing of the inertial parameter $I_{end}$ of the end of upper limbs of human body and the weights $a_0 \ldots a_p$ and $b_0 \ldots b_p$ of the $0 \ldots$ P-th-order function, $\varphi(t)$ is the matrix composing of the variables $x_g(i, t)$ and $\dot{x}_g(i, t)$, and the second-order derivative $\ddot{x}(t)$ of the displacement of the end of upper limbs of human body, $\hat{f}_m^n(t)$ is the estimated value of measured force of the n-th iteration, $\hat{f}_v^n(t)$ is the estimated value of the dynamic interaction force of the n-th iteration, $\hat{f}_r^n(t)$ is the estimated value of the restoring force of the n-th iteration; i and j are the order of the function, and t is time.

Figure 4:
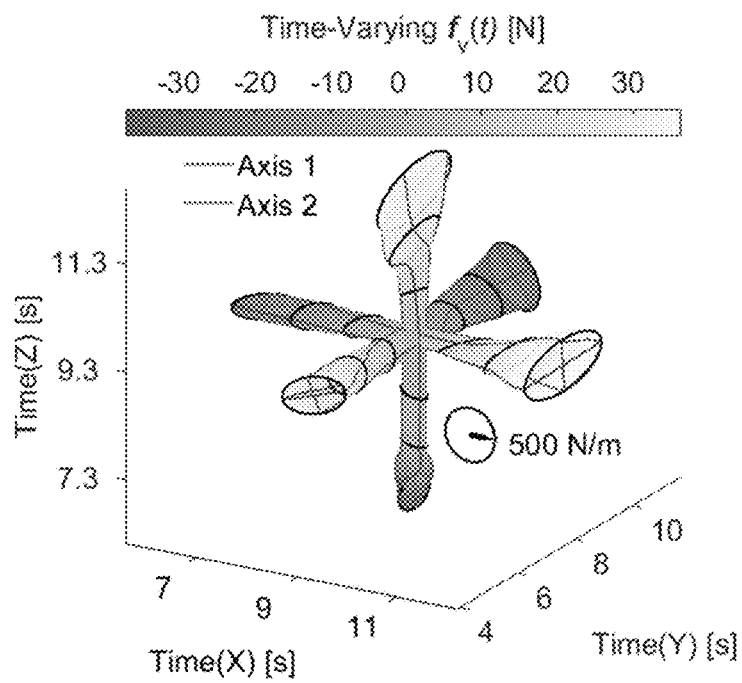
FIG. 4 is a schematic view of a time-varying stiffness ellipsoid of an upper limb end provided by an embodiment of the present disclosure.
Figure 5:
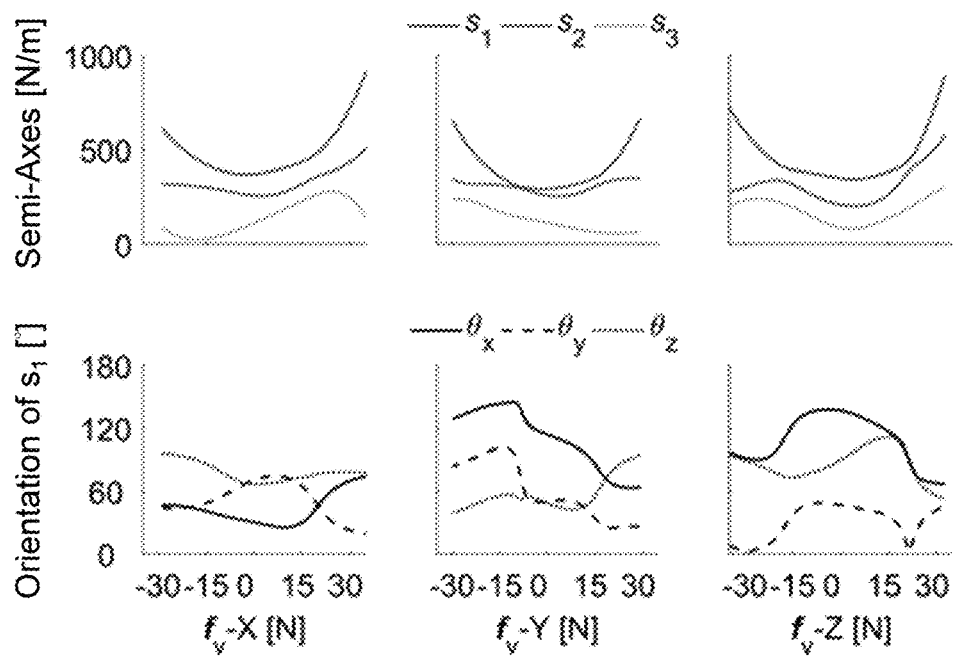
FIG. 5 is a schematic view of a time-varying stiffness curve of an upper limb end provided by an embodiment of the present disclosure.

After the above iterative identification algorithms are performed, the parameters in the parameter $\beta$, various restoring force $f_r(t)$ and dynamic interaction force $f_v(t)$ are obtained, and the above data is transmitted back to formula (3), so that the time-varying stiffness $K_{end}(t)$ of the end of upper limbs in the dynamic interaction process may be obtained. By performing singular value decomposition on the obtained stiffness matrix, the schematic view of the stiffness ellipsoid of the end of upper limbs shown in FIG. 4 and the curve diagram K (t) of the stiffness of the end of upper limbs shown in FIG. 5 are obtained.

Compared with the conventional technology, the present disclosure has the following advantages:

The dynamic interaction-oriented subject's limb time-varying stiffness identification method provided by the present disclosure is constructed based on the linear parameter varying method, the basis function expansion method and the iterative parameter identification method of the subject's limb time-varying stiffness identification method. The time-varying stiffness research problem of subject's limbs is transformed into a time-invariant research problem through the linear parameter varying method, thereby providing a new idea for the identification of time-varying stiffness. The provided iterative parameter identification can completely and accurately identify the time-varying stiffness of the subject's limbs by means of data in single perturbation, which significantly reduces complexity of the time-varying stiffness research. More importantly, the disclosure breaks through the limitation that the existing time-varying stiffness identification technology relying on single experimental data cannot be applied to the dynamic interaction with the environment. Generally speaking, the method for identifying the time-varying stiffness of a subject's limb provided by the present disclosure improves the accuracy of the time-varying stiffness identifying technique.

The motion data acquisition method for the time-varying stiffness identification of the subject's limb provided by the present disclosure can uniformly guide the experimental data acquisition of the time-varying stiffness research of the endpoint or joint of the subject's limb. The experimental paradigm is simple, the operability is high, and the stiffness characteristics of the endpoint or joint of the subject's limb can be completely changed. Moreover, the recorded data enables accurate resolution of the time-varying stiffness of the subject's limbs.

The present disclosure utilizes a multi-degree-of-freedom cooperative robotic arm to construct a small-perturbation environment to measure the time-varying stiffness of the subject's limb, thereby saving the complicated process of developing a special-purpose measuring device, reducing the difficulty of measuring the time-varying stiffness of the subject's limb, and expanding the application scenario of using the cooperative robotic arm for stiffness measurement, so that the time-varying stiffness measurement of the upper and lower limbs of the subject can be studied with the assistance of the cooperative robotic arm.

Those skilled in the art can easily understand that the above descriptions are only preferred embodiments of the present disclosure, and are not intended to limit the present disclosure. Any modifications, equivalent replacements and improvements made within the spirit and principles of the present disclosure, etc. should all be included within the protection scope of the present disclosure.

What is claimed is:

1. A dynamic interaction-oriented subject's limb time-varying stiffness identification method, comprising the following steps:
   in a random small-perturbation motion environment, a subject keeping a limb posture unchanged, and by changing states of muscles, a combination of a subject's limb displacement and a measured force data or a combination of an angle and a measured torque data being collected by a data acquisition system;
   based on a restoring force/torque expression with substituted time-varying impedance parameters and an expression of a dynamic interaction force/torque expanded by a basis function, and according to the combination of the subject's limb displacement and the measured force data or the combination of the angle and the measured torque data, iterative identification of the dynamic interaction force/torque and a restoring force/torque being performed by using parameters of time-varying dynamics;
   a linear coefficient matrix and the dynamic interaction force/torque obtained in the iterative identification of the parameters being utilized to calculate a time-varying stiffness of the subject's limb according to the restoring force/torque expression with the substituted time-varying impedance parameters;
   wherein the method for obtaining the restoring force/torque expression with the substituted time-varying impedance parameters comprises the following steps:
   according to time-varying impedance characteristics of the subject's limb, a second-order impedance model being utilized to construct a time-varying dynamic model of the subject's limb;
   a linear parameter varying method being adopted to construct a time-varying damping parameter of the subject's limb and the time-varying stiffness parameter of the subject's limb in the time-varying dynamic model of the subject's limb as a weighted sum of a function with a scheduling variable as an independent variable, and the restoring force/torque being transformed to obtain the restoring force/torque expression with the substituted time-varying impedance parameters; wherein the dynamic interaction force/torque is the scheduling variable;
   the method for obtaining the expression of the dynamic interaction force/torque expanded by the basis function is:
   the dynamic interaction force/torque being expressed by an expansion of the basis function, and a basis function sequence in a perturbation duration interval and weights of the basis function being utilized to represent the dynamic interaction force/torque,
   wherein the data acquisition system comprises a collaborative robotic arm, reflective markers, an optical motion capture system, a six-dimensional force/torque sensor and a display, wherein
   a tool end of the collaborative robotic arm is fixedly provided with the reflective markers, and is connected with the six-dimensional force/torque sensor, which is fixedly connected to an endpoint/joint of the limb when in use;
   the optical motion capture system is configured to collect a three-dimensional position of the reflective markers and obtain the displacement/angle information of the subject's limb;
   the reflective markers are configured to record the limb posture;
   the collaborative robotic arm is configured to construct the random small-perturbation motion environment in a three-dimensional space;
   the six-dimensional force/torque sensor is configured to collect a measured force/torque information between the subject's limb and the tool end of the robotic arm;
   the display provides the subject with visual feedback of real-time data from the six-dimensional force/torque sensor during dynamic interactions.

2. The dynamic interaction-oriented subject's limb time-varying stiffness identification method according to claim 1, wherein the method performs the iterative identification of the dynamic interaction force/torque and the restoring force/torque by using time-varying dynamic parameters comprises the following steps:
   (1) collected subject's limb displacement being combined with the measured force data or the angle being combined with the measured torque data, and initialize an estimated value of an initial restoring force/torque as 0;
   (2) based on the combination of the subject's limb displacement and the measured force data or the combination of the angle and the measured torque data, combined with an estimated value of the restoring force/torque under a current iteration, and according to the fact that a measured force/torque being equal to a sum of the restoring force/torque and the dynamic interaction force/torque, an g of the dynamic interaction force/torque being obtained;
   (3) according to the expression of the dynamic interaction force/torque expanded by the basis function, an intermediate variable of the dynamic interaction force/torque being utilized to identify the weights of the basis function;

(4) an estimated value of the dynamic interaction force/torque under the current iteration being obtained by using the weights of the basis function and the sequence of the basis functions in the perturbation duration interval;

(5) according to the fact that the measured force/torque being equal to the sum of the restoring force/torque and the dynamic interaction force/torque, an intermediate variable of the restoring force/torque being obtained;

(6) based on the restoring force/torque expression with the substituted time-varying impedance parameters, the intermediate variable of the restoring force/torque being utilized to obtain the linear coefficient matrix;

(7) according to a displacement parameter matrix and the linear coefficient matrix obtained under the current iteration, the estimated value of the restoring force/torque under the current iteration being obtained;

(8) return to step (2) until an actual number of the iterations reaches a predetermined maximum number of the iterations, and the linear coefficient matrix, the estimated value of the restoring force/torque and the estimated value of the dynamic interaction force/torque obtained in the last iteration being output.

3. The dynamic interaction-oriented subject's limb time-varying stiffness identification method according to claim 1, wherein the method for collecting the combination of the subject's limb displacement and the measured force data or the combination of the angle and the measured torque data is as follows:

in the random small-perturbation motion environment, the subject's limb keeping the limb posture unchanged, and an endpoint or a joint of the subject's limbs being connected with a collaborative robotic arm;

in the perturbation duration interval, the subject's limb completing at least one dynamic force/torque interaction cycle, and the combination of the subject's limb displacement and the force data or the combination of the angle and the torque data being collected;

wherein a dynamic force/torque being a regular interaction force/torque in a manner of, in three directions/rotation axes of X, Y and Z of the collaborative robotic arm, increasing a positive interaction force/torque first and reducing the positive interaction force/torque to 0, and then increasing a negative interaction force/torque and reducing the negative interaction force/torque to 0.

4. The dynamic interaction-oriented subject's limb time-varying stiffness identification method according to claim 1, wherein the restoring force/torque expression with the substituted time-varying impedance parameters is:

$$f_r(t)=\varphi(t)\beta\phi(t)=[\ddot{x}(t)\dot{x}_g(0,t)\dot{x}_g(1,t) \ldots \dot{x}_g(P,t)x_g(0,t)x_g(1,t) \ldots x_g(P,t)]\beta=[I\ b_0b_1 \ldots b_Pa_0a_1 \ldots a_P]^T$$

wherein I is an inertial parameter of the subject's limb, $g_i(f_v(t))$ is a function with the dynamic interaction force/torque $f_v(t)$ as the independent variable, $a_0 \ldots a_p$ and $b_0 \ldots b_p$ are weights of a 0 ... P-th-order function, P is the maximum order of the function, $f_r(t)$ is the restoring force/torque of the subject's limb, x(t) is a displacement/angle of the subject's limb collected by an optical motion capture system, β is a linear coefficient matrix composing of the inertial parameter I of the subject's limbs and the weights $a_0 \ldots a_p$ and $b_0 \ldots b_p$ of the 0 ... P-th-order function, φ(t) is a displacement/angle parameter matrix consisting of variables $x_g(i, t)$ and $\dot{x}_g(i, t)$, and a second-order derivative $\ddot{x}(t)$ of the displacement/angle of the subject's limb, $x_g(i, t)$ is an intermediate variable constructed from the function $g_i(f_v(t))$ and the displacement/angle x(t) of the subject's limb, $\dot{x}_g(i, t)$ is an intermediate variable constructed from the function $g_i(f_v(t))$ and a first-order derivative $\dot{x}(t)$ of the displacement/angle of the subject's limb, i is the order of a $g_i$ function, and t is time.

5. The dynamic interaction-oriented subject's limb time-varying stiffness identification method according to claim 1, wherein the expression of the dynamic interaction force/torque expanded by using the basis function is as follows:

$$f_v(t) = \sum_{j=0}^{Q} c_j h_j(t)$$

wherein $f_v(t)$ is the dynamic interaction force, $h_j(t)$ is the basis function sequence in the perturbation duration interval, $c_j$ represents a weight of the j-th-order basis function, Q is the maximum order of the basis function; and t is time.

6. A dynamic interaction-oriented subject's limb time-varying stiffness identification device, comprising: a data acquisition system, a restoring force/torque expression acquisition system, an iterative parameter identification system, and a dynamic interaction force/torque expression acquisition system, wherein the data acquisition system is configured to collect a combination of a subject's limb displacement and a measured force data or a combination of an angle and a measured torque data by changing states of muscles in a random small-perturbation motion environment, and the subject keeps a limb posture unchanged;

the restoring force/torque expression acquisition system is configured to reconstruct a restoring force/torque expression by substituting a time-varying impedance parameter of the subject's limb with a linear parameter varying method according to a time-varying dynamic system of the subject's limb;

the iterative parameter identification system is configured to, based on the restoring force/torque expression with the substituted time-varying impedance parameters and an expression of a dynamic interaction force/torque expanded by a basis function, and according to subject's limb displacement/angle information and measured force/torque information, perform iterative identification of the dynamic interaction force/torque and the restoring force/torque by using parameters of time-varying dynamics;

the dynamic interaction force/torque expression acquisition system is configured to expand the dynamic interaction force/torque using the basis function, and the dynamic interaction force/torque is represented by the basis function sequence in a perturbation duration interval and weights of the basis function, wherein the data acquisition system comprises a collaborative robotic arm, reflective markers, an optical motion capture system, a six-dimensional force/torque sensor and a display, wherein a tool end of the collaborative robotic arm is fixedly provided with the reflective markers, and is connected with the six-dimensional force/torque sensor, which is fixedly connected to an endpoint/joint of the limb when in use;

the optical motion capture system is configured to collect a three-dimensional position of the reflective markers and obtain the displacement/angle information of the subject's limb;

the reflective markers are configured to record the limb posture;

the collaborative robotic arm is configured to construct the random small-perturbation motion environment in a three-dimensional space;

the six-dimensional force/torque sensor is configured to collect the measured force/torque information between the subject's limb and the tool end of the robotic arm;

the display provides the subject with visual feedback of real-time data from the six-dimensional force/torque sensor during dynamic interactions.

7. The dynamic interaction-oriented subject's limb time-varying stiffness identification device according to claim 6, wherein the method for the restoring force/torque expression acquisition system to obtain the restoring force/torque expression with the substituted time-varying impedance parameters comprises the following steps:

according to time-varying impedance characteristics of the subject's limb, a second-order impedance model being utilized to construct a subject's limb time-varying dynamic model;

a linear parameter varying method being adopted to construct a time-varying damping parameter of the subject's limb and the time-varying stiffness parameter of the subject's limb in a dynamic model as a weighted sum of a function with a scheduling variable as an independent variable, and the restoring force/torque being transformed to substitute the time-varying impedance parameters; wherein the dynamic interaction force/torque is the scheduling variable.

8. The dynamic interaction-oriented subject's limb time-varying stiffness identification device according to claim 6, wherein the restoring force/torque expression with the substituted time-varying impedance parameters is:

$$f_r(t)=\varphi(t)\beta\varphi(t)=[\ddot{x}(t)\dot{x}_g(0,t)\dot{x}_g(1,t) \ldots \dot{x}_g(P,t)x_g(0,t)x_g(1,t) \ldots x_g(P,t)]\beta=[I\ b_0 b_1 \ldots b_P a_0 a_1 \ldots a_P]^T$$

wherein I is an inertial parameter of the subject's limb, $g_i(f_v(t))$ is a function with the dynamic interaction force/torque $f_v(t)$ as the independent variable, $a_0 \ldots a_p$ and $b_0 \ldots b_p$ are weights of a $0 \ldots$ P-th-order function, P is the maximum order of the function, $f_r(t)$ is the restoring force/torque of the subject's limb, x(t) is a displacement/angle of the subject's limb collected by an optical motion capture system, β is a linear coefficient matrix composing of the inertial parameter I of the subject's limbs and the weights $a_0 \ldots a_p$ and $b_0 \ldots b_p$ of the $0 \ldots$ P-th-order function, φ(t) is a displacement parameter matrix consisting of variables $x_g(i, t)$ and $\dot{x}_g(i, t)$, and a second-order derivative ẍ(t) of the displacement/angle of the subject's limb, $x_g(i, t)$ is an intermediate variable constructed from the function $g_i(f_v(t))$ and the displacement/angle x(t) of the subject's limb, $\dot{x}_g(i, t)$ is an intermediate variable constructed from the function $g_i(f_v(t))$ and a first-order derivative ẋ(t) of the displacement/angle of the subject's limb, i is the order of a $g_i$ function, and t is time;

the expression of the dynamic interaction force/torque expanded by using the basis function is as follows:

$$f_v(t) = \sum_{j=0}^{Q} c_j h_j(t)$$

wherein $f_v(t)$ is the dynamic interaction force, $h_j(t)$ is the basis function sequence in the perturbation duration interval, $c_j$ represents a weight of the j-th-order basis function, Q is the maximum order of the basis function; and t is time.

9. The dynamic interaction-oriented subject's limb time-varying stiffness identification device according to claim 6, wherein the method for the iterative parameter identification system to perform iterative identification of the dynamic interaction force/torque and the restoring force/torque comprises the following steps:

(1) the collected subject's limb displacement being combined with the measured force data or the angle being combined with the measured torque data, and initialize an estimated value of an initial restoring force/torque as 0;

(2) based on the combination of the subject's limb displacement and the measured force data or the combination of the angle and the measured torque data, combined with an estimated value of the restoring force/torque under a current iteration, and according to the fact that a measured force/torque being equal to a sum of the restoring force/torque and the dynamic interaction force/torque, an intermediate variable of the dynamic interaction force/torque being obtained;

(3) according to the expression of the dynamic interaction force/torque expanded by the basis function, the intermediate variable of the dynamic interaction force/torque being utilized to identify the weights of the basis function;

(4) an estimated value of the dynamic interaction force/torque under the current iteration being obtained by using the weights of the basis function and the sequence of the basis functions in the perturbation duration interval;

(5) according to the fact that the measured force/torque being equal to the sum of the restoring force/torque and the dynamic interaction force/torque, an intermediate variable of the restoring force/torque being obtained;

(6) based on the restoring force/torque with the substituted time-varying impedance parameters, the intermediate variable of the restoring force/torque being utilized to obtain the linear coefficient matrix;

(7) according to a displacement parameter matrix and the linear coefficient matrix obtained under the current iteration, the estimated value of the restoring force/torque under the current iteration being obtained;

(8) return to step (2) until an actual number of the iterations reaches a predetermined maximum number of the iterations, and the linear coefficient matrix, the estimated value of the restoring force/torque and the estimated value of the dynamic interaction force/torque obtained in the last iteration being output.

10. The dynamic interaction-oriented subject's limb time-varying stiffness identification method according to claim 2, wherein the method for collecting the combination of the subject's limb displacement and the measured force data or the combination of the angle and the measured torque data is as follows:

in the random small-perturbation motion environment, the subject's limb keeping the limb posture unchanged, and an endpoint or a joint of the subject's limbs being connected with a collaborative robotic arm;

in the perturbation duration interval, the subject's limb completing at least one dynamic force/torque interaction cycle, and the combination of the subject's limb displacement and the force data or the combination of the angle and the torque data being collected;

wherein a dynamic force/torque being a regular interaction force/torque in a manner of, in three directions/rotation axes of X, Y and Z of the collaborative robotic arm, increasing a positive interaction force/torque first and reducing the positive interaction force/torque to 0, and then increasing a negative interaction force/torque and reducing the negative interaction force/torque to 0.

11. The dynamic interaction-oriented subject's limb time-varying stiffness identification device according to claim 7, wherein the restoring force/torque expression with the substituted time-varying impedance parameters is:

$$f_r(t)=\varphi(t)\beta\varphi(t)=[\ddot{x}(t)\dot{x}_g(0,t)\dot{x}_g(1,t) \ldots \dot{x}_g(P,t)x_g(0,t)x_g(1,t) \ldots x_g(P,t)]\beta=[I\ b_0 b_1 \ldots b_P a_0 a_1 \ldots a_P]^T$$

wherein I is an inertial parameter of the subject's limb, $g_i(f_v(t))$ is a function with the dynamic interaction force/torque $f_v(t)$ as the independent variable, $a_0 \ldots a_p$ and $b_0 \ldots b_p$ are weights of a 0 ... P-th-order function, P is the maximum order of the function, $f_r(t)$ is the restoring force/torque of the subject's limb, x(t) is a displacement/angle of the subject's limb collected by an optical motion capture system, β is a linear coefficient matrix composing of the inertial parameter I of the subject's limbs and the weights $a_0 \ldots a_p$ and $b_0 \ldots b_p$ of the 0 ... P-th-order function, φ(t) is a displacement parameter matrix consisting of variables $x_g(i, t)$ and $\dot{x}_g(i, t)$, and a second-order derivative $\ddot{x}(t)$ of the displacement/angle of the subject's limb, $x_g(i, t)$ is an intermediate variable constructed from the function $g_i(f_v(t))$ and the displacement/angle x(t) of the subject's limb, $\dot{x}_g(i, t)$ is an intermediate variable constructed from the function $g_i(f_v(t))$ and a first-order derivative $\dot{x}(t)$ of the displacement/angle of the subject's limb, i is the order of a $g_i$ function, and t is time;

the expression of the dynamic interaction force/torque expanded by using the basis function is as follows:

$$f_v(t) = \sum_{j=0}^{Q} c_j h_j(t)$$

wherein $f_v(t)$ is the dynamic interaction force, $h_j(t)$ is the basis function sequence in the perturbation duration interval, $c_j$ represents a weight of the j-th-order basis function, Q is the maximum order of the basis function; and t is time.

* * * * *